US008107698B2

(12) United States Patent  (10) Patent No.: US 8,107,698 B2
Kitamura  (45) Date of Patent: Jan. 31, 2012

(54) IMAGE PROCESSING APPARATUS AND COMPUTER PROGRAM PRODUCT

(75) Inventor: Makoto Kitamura, Tokyo (JP)

(73) Assignee: Olympus Corporation, Tokyo (JP)

( * ) Notice: Subject to any disclaimer, the term of this patent is extended or adjusted under 35 U.S.C. 154(b) by 958 days.

(21) Appl. No.: 12/105,006

(22) Filed: Apr. 17, 2008

(65) Prior Publication Data
US 2008/0279431 A1  Nov. 13, 2008

(30) Foreign Application Priority Data

May 8, 2007 (JP) ................................. 2007-123824
May 8, 2007 (JP) ................................. 2007-123825

(51) Int. Cl.
G06K 9/00 (2006.01)
H04N 7/18 (2006.01)
(52) U.S. Cl. ......................................... 382/128; 345/65
(58) Field of Classification Search ........................ None
See application file for complete search history.

(56) References Cited

U.S. PATENT DOCUMENTS

| 2004/0225223 | A1  |   | 11/2004 | Honda et al. |         |
|--------------|-----|---|---------|--------------|---------|
| 2008/0086028 | A1  | * | 4/2008  | Matsui       | 348/45  |
| 2010/0045786 | A1  | * | 2/2010  | Kitamura     | 382/128 |
| 2010/0092055 | A1  | * | 4/2010  | Matsuda      | 382/128 |
| 2010/0208047 | A1  | * | 8/2010  | Kitamura     | 382/128 |
| 2010/0259650 | A1  | * | 10/2010 | Sasaki       | 382/275 |
| 2011/0069876 | A1  | * | 3/2011  | Kanda        | 382/128 |

FOREIGN PATENT DOCUMENTS

| EP | 1 849 402 A1    | 10/2007 |
|----|-----------------|---------|
| JP | 7-323024        | 12/1995 |
| JP | 2004-521693     | 7/2004  |
| JP | 2004-337596     | 12/2004 |
| JP | 2005-192880     | 7/2005  |
| WO | WO 02/073507 A2 | 9/2002  |
| WO | WO 2006/087981 A1 | 8/2006 |

* cited by examiner

*Primary Examiner* — Jermele M Hollington
(74) *Attorney, Agent, or Firm* — Scully, Scott, Murphy & Presser, P.C.

(57) ABSTRACT

An image processing apparatus includes an organ determination unit that determines a type of observation target which appears in a target image among a sequence of observation images, an imaging distance estimation unit that estimates an imaging distance at a time of image pickup of the observation image, an abnormal region detection unit that detects an abnormal region, which is a specific region, from the target image using an abnormality detection parameter, and an image processing control unit that sets as the abnormality detection parameter, a parameter value corresponding to a result of determination by the organ determination unit, and causes the abnormal region detection unit to detect an abnormal region using the abnormality detection parameter.

20 Claims, 15 Drawing Sheets

FIG.7

|  | ABNORMALITY DETECTION PARAMETER (SIZE PARAMETER) | | |
|---|---|---|---|
|  | STOMACH | SMALL INTESTINE | LARGE INTESTINE |
| IMAGING DISTANCE | 0.1 | 1.0 | 0.6 | 0.8 |
|  | 0.2 | 0.8 | 0.5 | 0.7 |
|  | . | . | . | . |
|  | . | . | . | . |
|  | 1.0 | 0.1 | 0.1 | 0.1 |

FIG.8

ORGAN DETERMINATION PROCESSING

↓

CALCULATE ENTROPY FOR EACH OBSERVATION IMAGE — S211

↓

CALCULATE OVERALL AVERAGE OF ENTROPY OF ALL OBSERVATION IMAGES — S212

↓

DETERMINE ORGAN WHOSE IMAGE IS PICKED UP IN EACH OBSERVATION IMAGE BASED ON ENTROPY, OVERALL AVERAGE THEREOF, AND ORGAN DETERMINATION REFERENCE DATA — S213

↓

RETURN

| ENTROPY | | OVERALL AVERAGE OF ENTROPY | | | | |
|---|---|---|---|---|---|---|
| | | 0.1 | 0.2 | . | . | 1.0 |
| | 0.1 | STOMACH | STOMACH | . | . | STOMACH |
| | 0.2 | SMALL INTESTINE | SMALL INTESTINE | . | . | STOMACH |
| | . | . | . | . | . | . |
| | . | . | . | . | . | . |
| | 1.0 | SMALL INTESTINE | SMALL INTESTINE | . | . | SMALL INTESTINE |

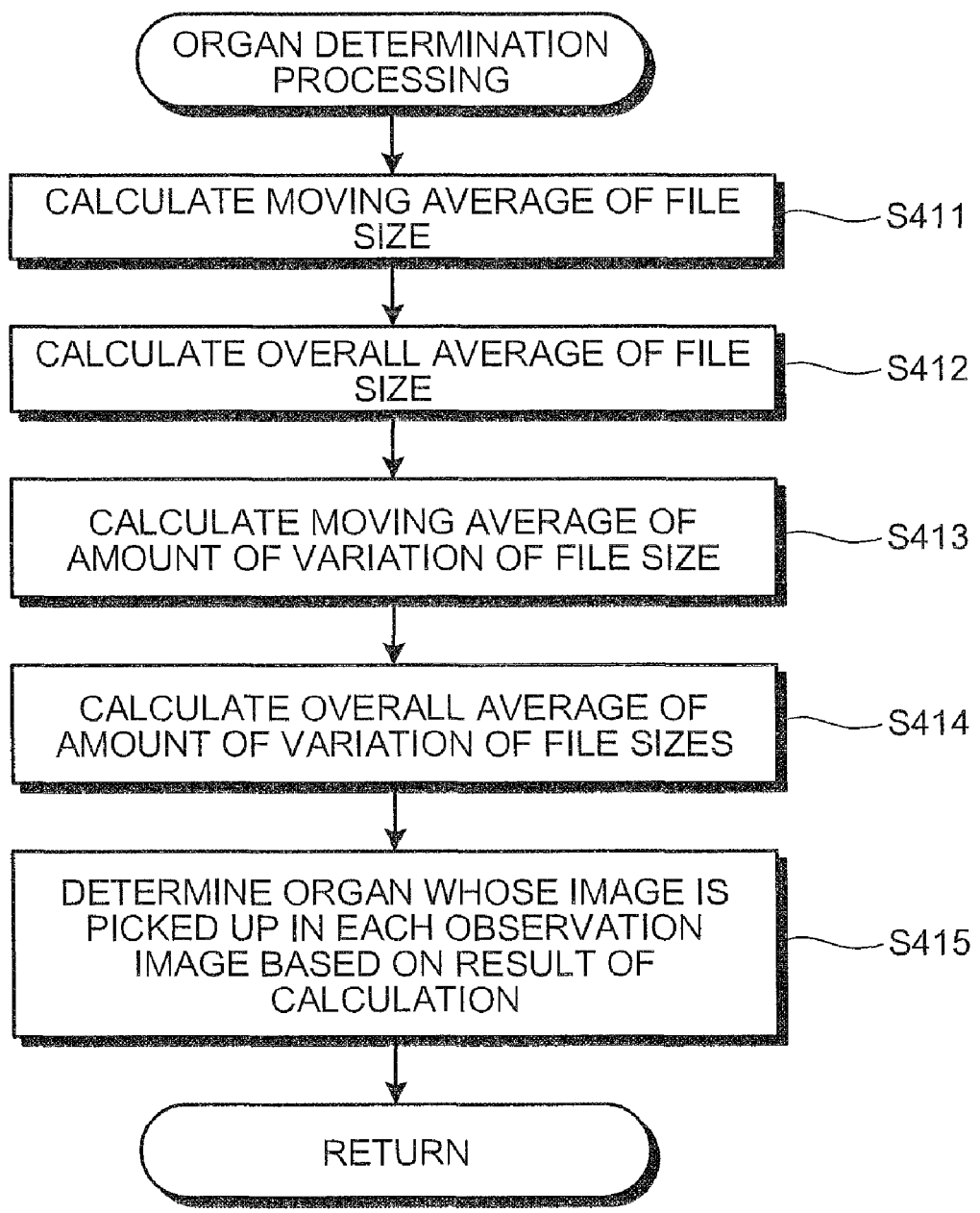

IMAGE NUMBER OF OBSERVATION IMAGES

IMAGE NUMBER OF OBSERVATION IMAGES

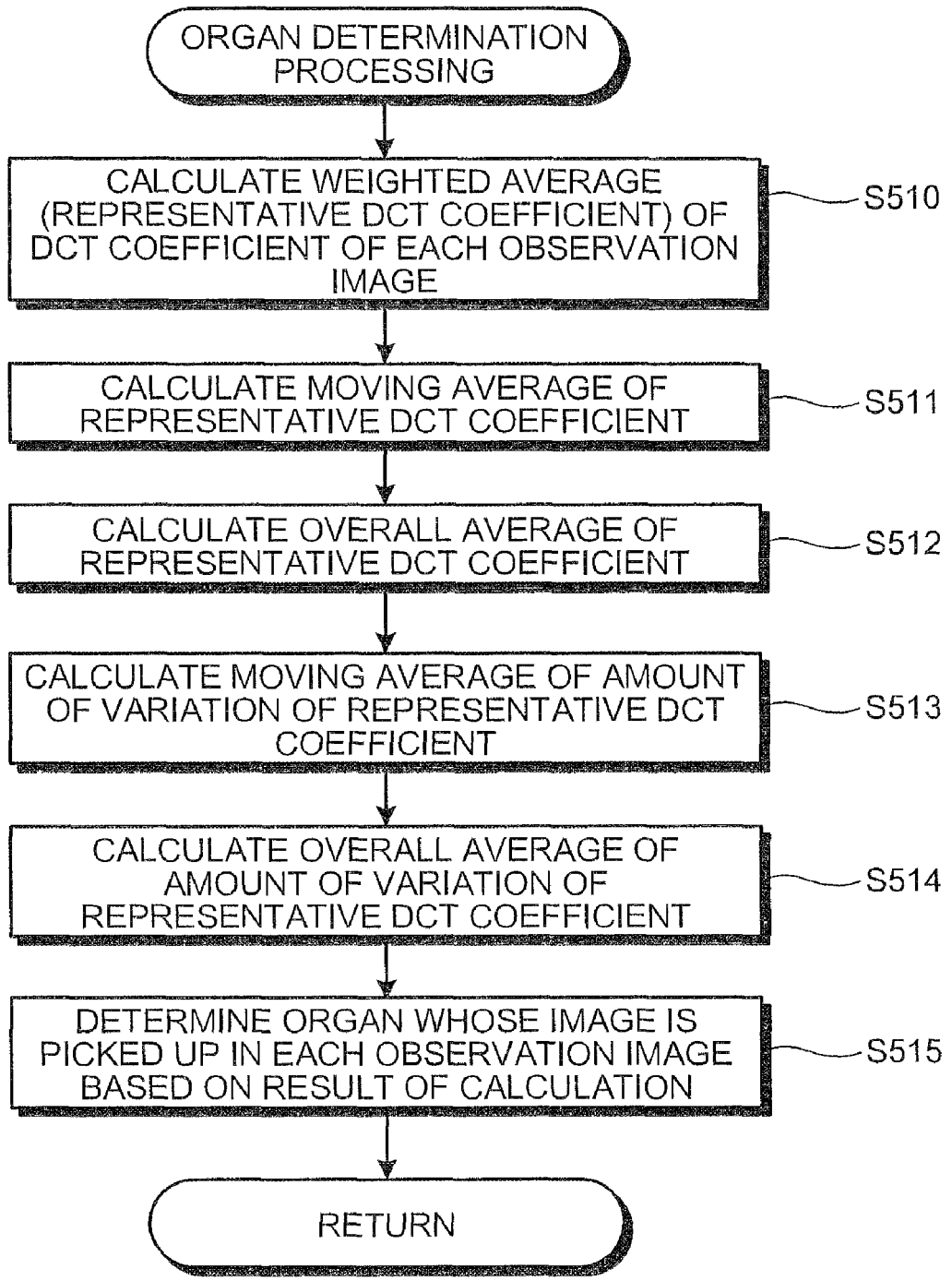

FIG.14

DC COMPONENT

| DCT 1 | DCT 2 | DCT 6 | DCT 7 | ... | | | |
|---|---|---|---|---|---|---|---|
| DCT 3 | DCT 5 | DCT 8 | ... | | | | |
| DCT 4 | DCT 9 | ... | | | | | |
| DCT 10 | ... | | | | | | |
| ... | | | | | | ... | DCT 55 |
| | | | | | ... | DCT 56 | DCT 61 |
| | | | | ... | DCT 57 | DCT 60 | DCT 62 |
| | | | ... | DCT 58 | DCT 59 | DCT 63 | DCT 64 |

FIG.17A

|  | ORGAN | | |
|---|---|---|---|
|  | STOMACH | SMALL INTESTINE | LARGE INTESTINE |
| ABNORMALITY DETECTION PARAMETER (SIZE PARAMETER) | 0.1 | 0.6 | 0.8 |

FIG.17B

|  |  | ABNORMALITY DETECTION PARAMETER (SIZE PARAMETER) |
|---|---|---|
| IMAGING DISTANCE | 0.1 | 1.0 |
|  | 0.2 | 0.8 |
|  | . | . |
|  | . | . |
|  | 1.0 | 0.1 |

IMAGE PROCESSING APPARATUS AND COMPUTER PROGRAM PRODUCT

CROSS-REFERENCE TO RELATED APPLICATIONS

This application is based upon and claims the benefit of priority from Japanese Patent Applications No. 2007-123824 and No. 2007-123825, both filed May 8, 2007, the entire contents of both of which are incorporated herein by reference.

BACKGROUND OF THE INVENTION

1. Field of the Invention

The present invention relates to an image processing apparatus for detecting a specific region in an observation image, and an image processing program which can be provided as a computer program product, and more particularly to an image processing apparatus and an image processing program for detecting a specific region in a sequence of observation images which individually show at least one observation target among plural types of observation targets, or a specific region in a sequence of observation images picked up from different imaging distances.

2. Description of the Related Art

As a system for obtaining a sequence of observation images which individually show at least one observation target among plural types of observation targets, a capsule endoscope, for example, which serves to observe an interior of a subject has been developed. The capsule endoscope has an imaging function and a radio communication function. After being swallowed by a subject, the capsule endoscope moves through the interior of esophagus, stomach, small intestine, large intestine, and the like, following peristaltic movements or the like while sequentially picking up images and sequentially transmitting image data generated by the image pickup to an external receiver by radio communication and the like until naturally discharged. Doctors, nurses, and the others can display the image data the external receiver acquires as an observation image and observe the interior of the subject based on the observation image.

Generally, the capsule endoscope acquires an enormous number of observation images in sequence, which demands doctors, nurses, and others to put significant amount of time and energy for the observation based on the sequence of observation images. Meanwhile, an abnormality detecting system (such as one described in Published Japanese Translation of International Patent Application No. 2004-521693 (Kohyo)) is developed to allow detection and display of abnormal areas in an observation target and efficient observation of affected areas based thereon. The abnormality detecting system divides observation images into plural unit blocks and compares color information of each unit block with a previously-prepared color reference of abnormal area and a previously-prepared color reference of normal area to detect abnormal areas.

In the sequence of observation images acquired by the capsule endoscope, each organ appears in significantly different brightness and color from other organs depending on its type; for example, the small intestine appears in murkier colors than the stomach because of the influence of mucus, content, and the like. Further, the characteristics of the abnormal area, which is a detection target, are different for each type of organ. For example, an enlarged blood vessel in the small intestine is an abnormal area which should be detected, while a blood vessel in the stomach is an abnormal area which does not need to be detected preferentially. Thus, some abnormal areas are organ-dependent.

In the sequence of observation images acquired by the capsule endoscope, each observation image of the same abnormal area in the organ is picked up from different imaging distance because the capsule endoscope, which serves as an imaging device, picks up the images while moving through the organs. Thus, image regions corresponding to the same abnormal area are in different sizes (areas) and colors in respective observation images according to the imaging distances, and thereby exhibit different features.

SUMMARY OF THE INVENTION

An image processing apparatus according to one aspect of the present invention is an image processing apparatus for detecting a feature image region, which is a specific region, from a sequence of observation images in which an image of at least one type of plural types of observation targets is picked up individually, and includes a target determination unit that determines a type of an observation target whose image is picked up in a target image among the sequence of observation images; a region detection unit that detects the feature image region from the target image using a process parameter for detecting the feature image region; a distance estimation unit that estimates an imaging distance at a time of image pickup of the target image; and a setting control unit that sets a parameter value corresponding to a result of determination by the target determination unit and a result of estimation by the distance estimation unit, as the process parameter, and causes the region detection unit to detect the feature image region using the process parameter.

Further, an image processing apparatus according to another aspect of the present invention is an image processing apparatus for detecting a feature image region, which is a specific region, from a sequence of observation images in which an image of at least one type of plural types of observation targets is picked up individually, and includes a target determination unit that determines a type of an observation target whose image is picked up in a target image in the sequence of observation images; a region detection unit that detects the feature image region in the target image using a process parameter for detecting the feature image region; and a setting control unit that sets a parameter value corresponding to a result of determination by the target determination unit as the process parameter, and causes the region detection unit to detect the feature image region using the process parameter.

Further, a computer program product according to still another aspect of the present invention is a computer program product having a computer readable medium including programmed instructions for detecting a feature image region, which is a specific region, from a sequence of observation images in which an image of at least one type of plural types of observation targets is picked up individually, wherein the instructions, when executed by a computer, cause the computer to perform determining a type of an observation target whose image is picked up in a target image among the sequence of observation images; setting a parameter value corresponding to a result of determination of the type of the observation target as a process parameter for detecting the feature image region; and detecting the feature image region from the target image using the process parameter set.

Further, an image processing apparatus according to still another aspect of the present invention is an image processing apparatus for detecting a feature image region, which is a specific region, from a sequence of observation images picked up at different imaging distances, and includes a distance estimation unit that estimates an imaging distance at a time of image pickup of a target image among the sequence of observation images; a region detection unit that detects the feature image region from the target image using a process parameter for detecting the feature image region; and a setting control unit that sets a parameter value corresponding to a result of estimation by the distance estimation unit as the process parameter, and causes the region detection unit to detect the feature image region using the process parameter.

Further, a computer program product according to still another aspect of the present invention is a computer program product having a computer readable medium including programmed instructions for detecting a feature image region, which is a specific region, from a sequence of observation images picked up at different imaging distances, wherein the instructions, when executed by a computer, cause the computer to perform estimating an imaging distance at a time of image pickup of a target image among the sequence of observation images; setting a parameter value corresponding to a result of estimation of the imaging distance as a process parameter for detecting the feature image region; and detecting the feature image region from the target image using the process parameter.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a table of parameter values stored in an abnormality detection parameter storage unit;

FIG. 8 is a flowchart of an organ determination processing procedures according to a first modification;

FIG. 11 is a flowchart of organ determination processing procedures according to a third modification;

FIG. 13 is a flowchart of organ determination processing procedures according to a fourth modification;

FIG. 14 is a diagram of DCT coefficients in an 8×8 pixel block;

FIG. 17A is a table of parameter values stored as abnormality detection parameters; and FIG. 17B is a table of parameter values stored as abnormality detection parameters.

DETAILED DESCRIPTION OF THE PREFERRED EMBODIMENTS

Figure 1:
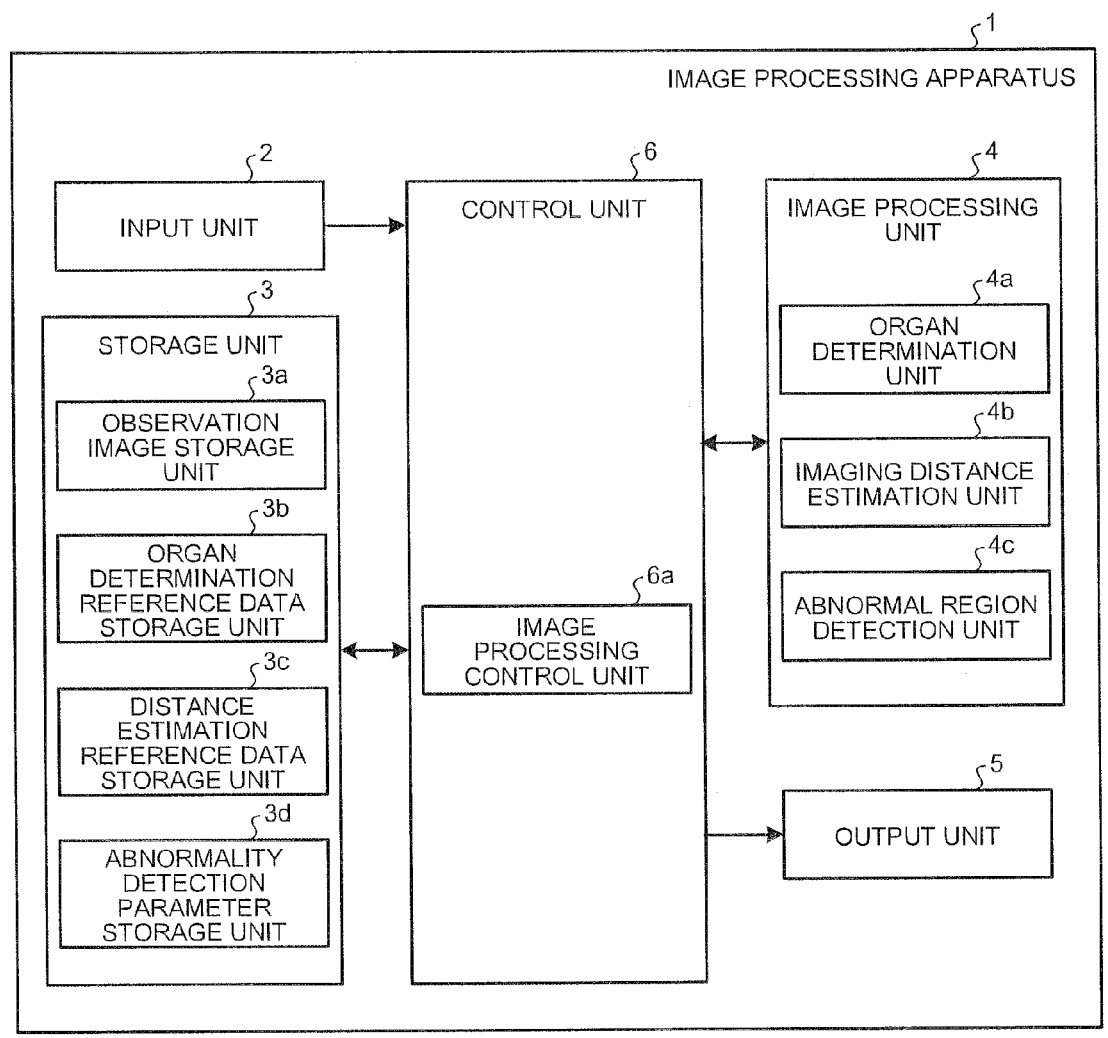
FIG. 1 is a block diagram of main units of an image processing apparatus according to one embodiment of the present invention.

Exemplary embodiments of an image processing apparatus and an image processing program according to the present invention are described in detail below with reference to the accompanying drawings. In the following embodiments, the image processing apparatus according to the present invention is described as an apparatus which processes a sequence of observation images obtained by a capsule endoscope through sequential image pickup of an interior of at least one organ in a group of organs consisting of esophagus, stomach, small intestine, and large intestine, as a sequence of observation images which individually show at least one observation target among plural types of observation targets. It should be noted, however, that the processible observation image of the image processing apparatus of the present invention is not limited to the observation image obtained through image pickup of organs (digestive tracts) as an observation target, and that the embodiments do not limit the present invention. In the drawings, same part is denoted by same reference character.

Firstly, the image processing apparatus according to one embodiment of the present invention is described. FIG. 1 is a block diagram of main units of an image processing apparatus 1 according to the embodiment. As shown in FIG. 1, the image processing apparatus 1 includes an input unit 2 which receives an input of various pieces of information such as an image, a storage unit 3 which stores information, and an output unit 5 which outputs information, an image processing unit 4 which processes an image stored in the storage unit 3, and a control unit 6 which is electrically connected to each of the above-mentioned units to control processing and operation of each connected unit.

The input unit 2 is configured with a data communication interface, and supplies via the data communication interface, image data of a sequence of observation images as a processing target to the control unit 6. Further, the input unit 2 is provided with various types of input devices so as to input various types of information such as parameter values of process parameters employed by the control unit 6 for the processing.

The storage unit 3 is configured with a hard disk, a ROM, a RAM, and the like, and stores various types of information such as various types of processing programs executed by the control unit 6, various types of process parameters employed by the control unit 6 for processing, and results of various types of processing performed by the control unit 6. More specifically, the storage unit 3 includes an observation image storage unit 3a which stores a sequence of observation images supplied by the input unit 2, an organ determination reference data storage unit 3b which stores reference data employed in organ determination processing described later, a distance estimation reference data storage unit 3c which stores reference data employed for imaging distance estimation processing described later, and an abnormality detection parameter storage unit 3d which stores parameter values of parameters employed in abnormal region detection processing described later. The storage unit 3 includes a portable recording medium which is attachable to and detachable from the image processing apparatus 1, so that the storage unit 3 can acquire the image data via the portable recording medium and not via the input unit 2 to store the sequence of observation images.

The image processing unit 4 is implemented, for example, by a CPU, so as to perform various types of image processing on the sequence of observation images stored in the observation image storage unit 3a based on a predetermined image processing program executed by the control unit 6. Specifically, the image processing unit 4 includes an organ determination unit 4a which determines a predetermined organ appears in each observation image as an observation target, an imaging distance estimation unit 4b which estimates an imaging distance at the time the observation image is picked up, and an abnormal region detection unit 4c which detects an abnormal region, which is a feature image region having a predetermined feature, in the observation image. More specifically, the organ determination unit 4a determines that an observation target appears in each observation image is an esophagus, a stomach, a small intestine, or a large intestine, and the abnormal region detection unit 4c detects an abnormal region which is an image region corresponding to an abnormal area in the organ determined by the organ determination unit 4a.

The output unit 5 is configured with various types of displays such as a liquid crystal display, and displays various types of information such as a sequence of observation images, a result of determination by the organ determination unit 4a, a result of estimation by the imaging distance estimation unit 4b, and a result of detection by the abnormal region detection unit 4c. Further, the output unit 5 includes a data communication interface and is capable of outputting various types of information to an external device via the data communication interface.

The control unit 6 is implemented by a CPU, and controls processing and operations of each unit provided in the image processing apparatus 1 by executing a predetermined processing program stored in the storage unit 3. Specifically, the control unit 6 includes an image processing control unit 6a which executes a predetermined image processing program stored in the storage unit 3 and causes the image processing unit 4 to process a sequence of observation images stored in the observation image storage unit 3a. Further, the control unit 6 causes the output unit 5 to output a result of processing by the image processing unit 4 and the like.

Figure 2:
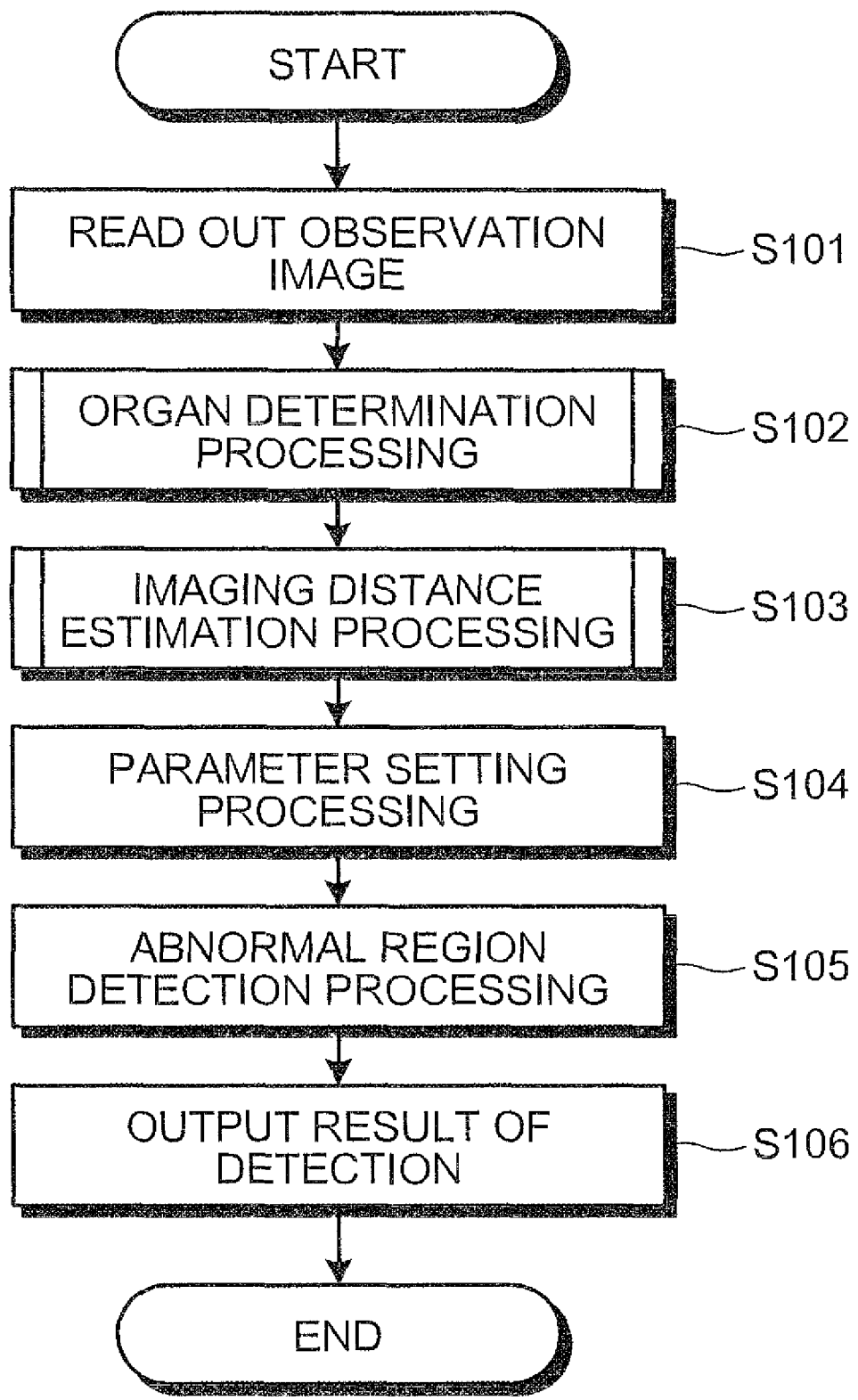
FIG. 2 is a flowchart of image processing procedures performed by the image processing apparatus.

Next, image processing procedures performed by the image processing apparatus 1 is described. FIG. 2 is a flowchart of processing procedures of processing of a sequence of observation images stored in the observation image storage unit 3a performed by the execution of a predetermined image processing program by the control unit 6. As shown in FIG. 2, the image processing control unit 6a first reads out the sequence of observation images from the observation image storage unit 3a (step S101), causes the organ determination unit 4a to perform the organ determination processing to determine the organ in each observation image (step S102), and causes the imaging distance estimation unit 4b to perform the imaging distance estimation processing to estimate the imaging distance at the time each observation image is picked up (step S103). Thereafter, the image processing control unit 6a performs parameter setting processing to set a parameter value of an abnormality detection parameter mentioned later based on the result of organ determination in the organ determination processing and the result of imaging distance estimation in the imaging distance estimation processing (step S104), and further performs abnormal region detection processing by causing the abnormal region detection unit 4c to detect the abnormal region using the abnormal detection parameter (step S105). Then, the image processing control unit 6a causes the output unit 5 to output the result of detection in the abnormal region detection processing (step S106) and finishes the sequence of processing.

In the organ determination processing in step S102, the organ determination unit 4a determines the organ whose image is picked up in each observation image based on frequency component information of the observation image. For example, the surface of mucous membranes of the esophagus and the stomach is less uneven and smoother than the surface of the small intestine. On the other hand, the small intestine has villus and the like and the surface there of is more uneven. Hence, the low frequency components are dominant in the observation image of esophagus and stomach, while the high frequency components are dominant in the observation image of small intestine. The organ determination unit 4a, utilizing such characteristics, determines whether the organ whose image is picked up in the observation image is the esophagus, stomach, small intestine, or large intestine. Specifically, the organ determination unit 4a performs the organ determination using power spectrum obtained by performing Fourier transform, for example, as the frequency component information.

Figure 3:
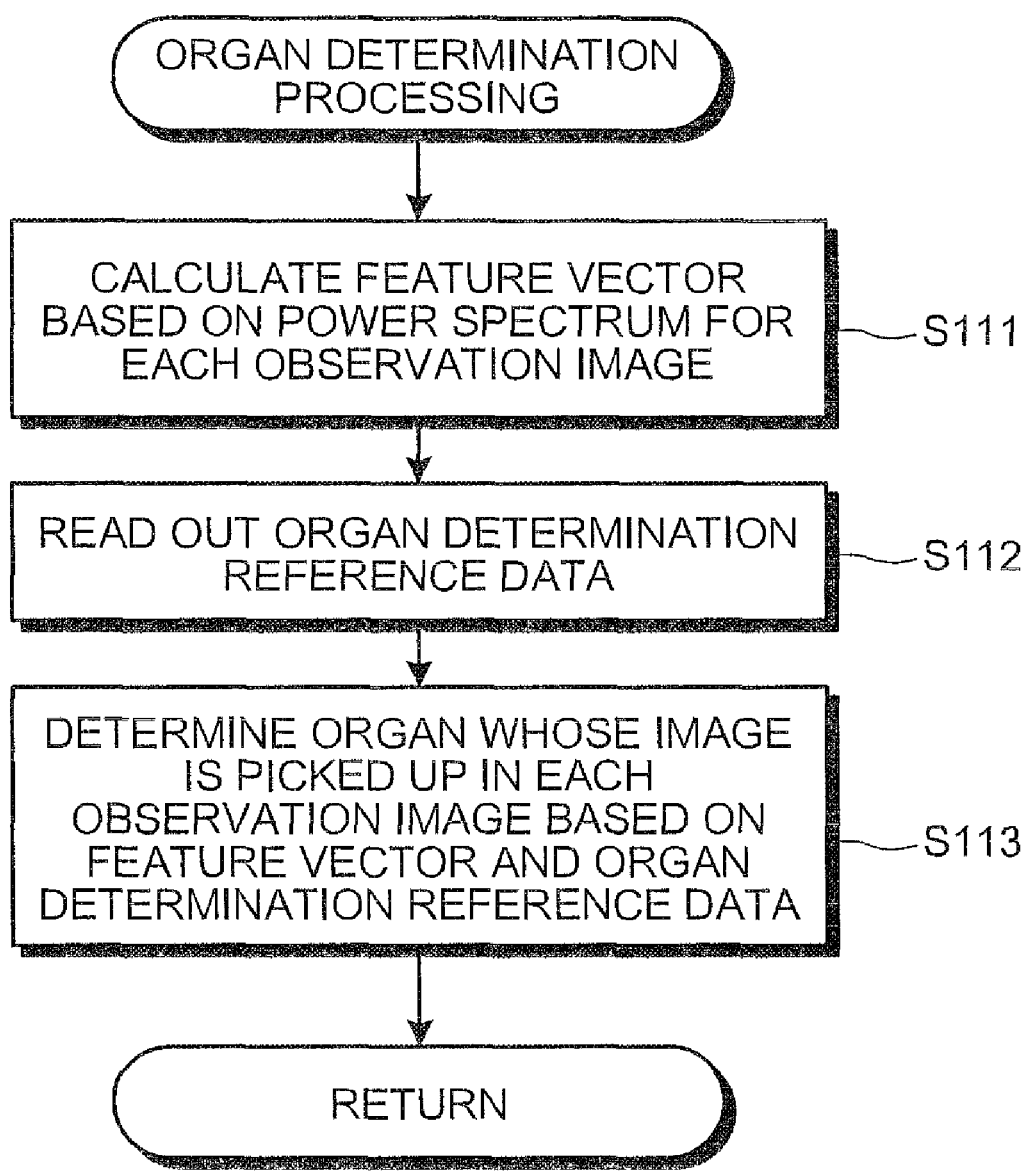
FIG. 3 is a flowchart of organ determination processing procedures.

FIG. 3 is a flowchart of the organ determination processing procedures performed by the organ determination unit 4a. As shown in FIG. 3, the organ determination unit 4a calculates a feature vector based on a power spectrum of each observation image (step S111), reads out organ determination reference data from the organ determination reference data storage unit 3b (step S112), and determines the organ whose image is picked up in each observation image based on the calculated feature vector and the read-out organ determination reference data (step S113). Thereafter, the organ determination unit 4a finishes the organ determination processing and returns to step S102.

In step S111, the organ determination unit 4a calculates by Fourier transform the power spectrum of a target image in the sequence of observation images, and extracts a high frequency component, an intermediate frequency component, and a low frequency component from the obtained power spectrum, respectively as feature quantities A, B, and C. Then, the organ determination unit 4a finds in a feature space a vector represented by the feature quantities A, B, and C, and associates the target image with the found vector as a feature vector representing the frequency component information of the target image. Further, the organ determination unit 4a sequentially switches the target image from one image to another of the sequence of observation images, and performs the processing described above to each target image, to thereby calculate a feature vector of each observation image.

Figure 4:
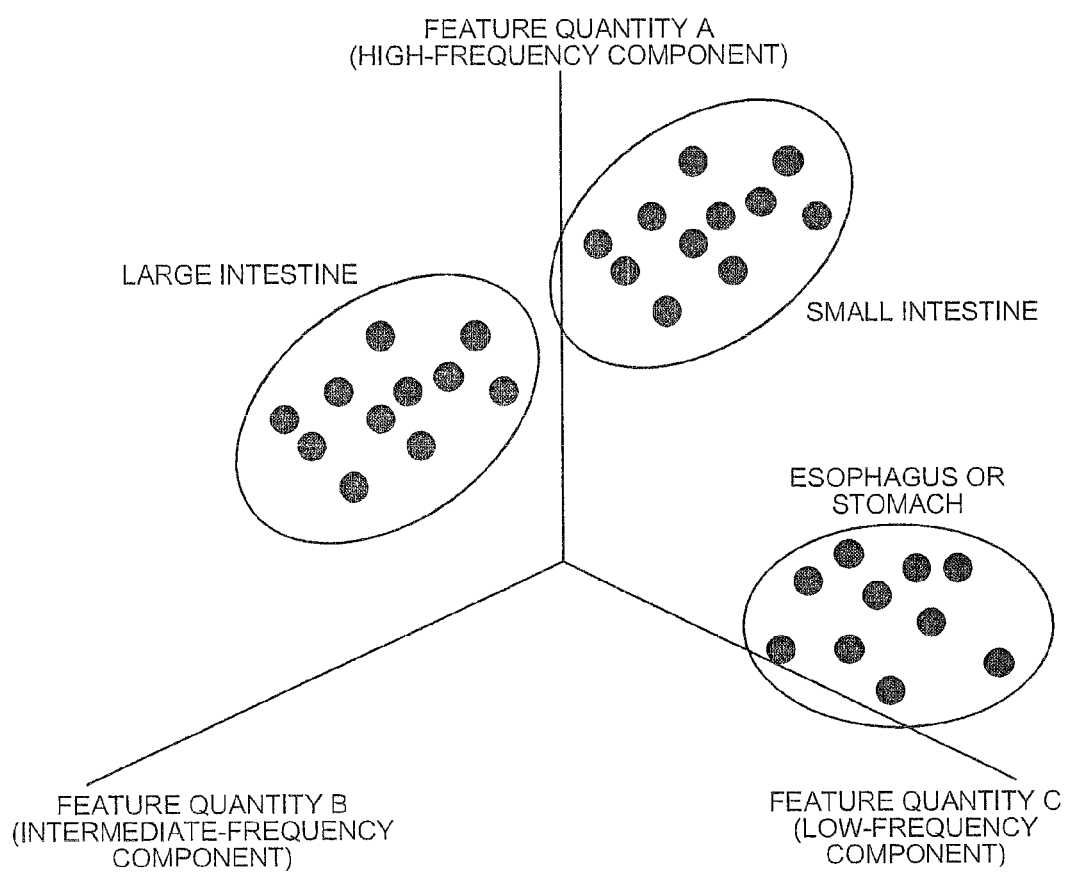
FIG. 4 is a diagram for explaining organ determination reference data.

In step S112, the organ determination unit 4a reads out the organ determination reference data as a class dictionary which classifies organs on the feature space in advance as shown in FIG. 4, for example. Then, in step S113, the organ determination unit 4a determines the type of organ to which the feature vector calculated in step S111 for each observation image belongs based on the organ determination reference data read out in step S112 using a known determination technique such as kNN method (k-Nearest Neighbor Method), and subspace method. In the determination, the organ determination unit 4a sequentially switches the target image from one image to another of the sequence of observation images and determines for each target image a type of organ to which the feature vector belongs. Thus, the organ determination unit 4a determines the organ whose image is picked up in each observation image as one of the esophagus, stomach, small intestine, and large intestine, and associates the result of determination with each observation image.

In the above, the organ determination is described as being performed based on the feature vector represented by three frequency components in the power spectrum. The number of frequency components employed as feature quantities, in other words, the number of dimensions of the feature quantity is not limited to three, and can be two, four or more. When the number of dimensions is four or more, the organ determination can be performed with higher accuracy. However, when the number of dimensions is four or more, processing time required for the organ determination increases. Hence, it is preferable to appropriately set the number of dimensions according to desired determination accuracy. In the above, the organ determination is performed by characterizing the power spectrum by the feature vector. The organ determination, however, can be performed without using the feature vector. For example, pattern matching can be performed on a distribution pattern of the power spectrum based on a reference distribution pattern prepared in advance for each organ.

In the imaging distance estimation processing in step S103, the imaging distance estimation unit 4b estimates the imaging distance at the time of image pickup of each observation image, in other words, the distance from the capsule endoscope or the like as the imaging device that picks up the observation image to an inner wall of the organ as the subject, based on brightness information or gain information of the observation image.

Figure 5:
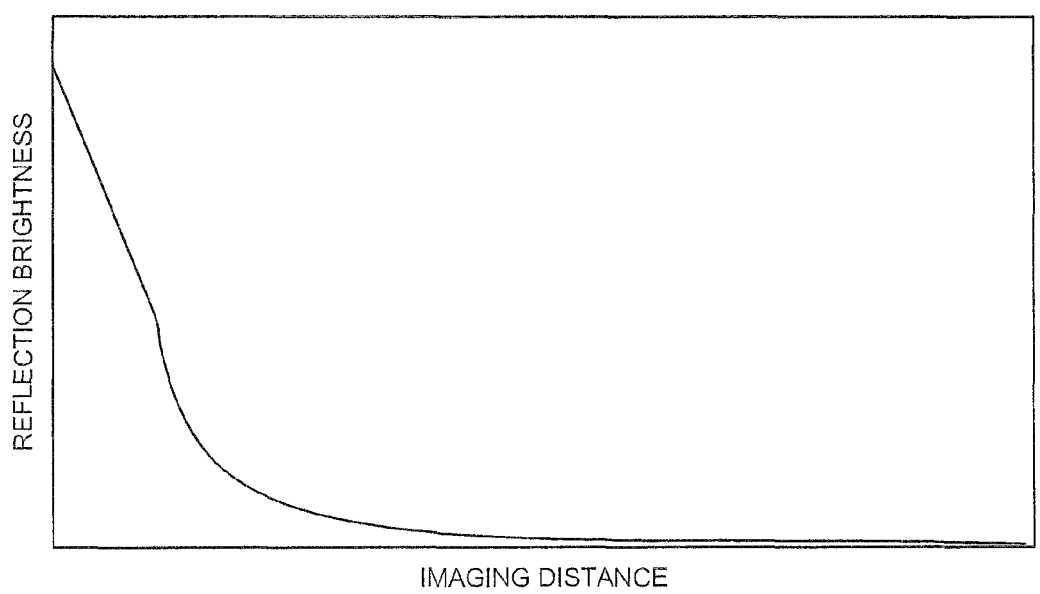
FIG. 5 is a graph of reflection brightness characteristic against imaging distance.

Generally in the observation image, the reflection brightness (or reflected brightness) changes according to the imaging distance. The reflection brightness is brightness of light received as observation light by the imaging device after the illumination light emitted from the imaging device or the like is reflected by the subject. The reflection brightness becomes higher as the subject comes close to the imaging device and becomes lower as the subject moves away from the imaging device. It is known that the reflection brightness is inversely proportional to the square of the imaging distance as shown in FIG. 5 which represents the relation between the imaging distance and the reflection brightness. As the reflection brightness becomes higher, the average brightness of the observation image becomes high, and as the reflection brightness becomes lower, the average brightness of the observation image becomes low. The imaging distance estimation unit 4b, utilizing this characteristic, estimates the imaging distance based on the average brightness of the observation image. Here, the average brightness of the observation image means an average value of brightness (pixel value) of all pixels in the observation image, or an average value of brightness (pixel value) of the predetermined plural number of pixels in the observation image.

When the imaging device has an AGC (Auto Gain Control) function, gain is generally corrected at the time of image pickup of the observation image according to the reflection brightness. Specifically, the gain control is performed so that the gain is decreased when the imaging distance is short and the reflection brightness is high, whereas the gain is increased when the imaging distance is long and the reflection brightness is low. The capsule endoscope generally has the AGC function, and records an AGC correction value which is a gain correcting value as additional information of each observation image. The imaging distance estimation unit 4b, utilizing the characteristic of the AGC function, estimates the imaging distance based on the AGC correction value recorded for each observation image.

Figure 6:
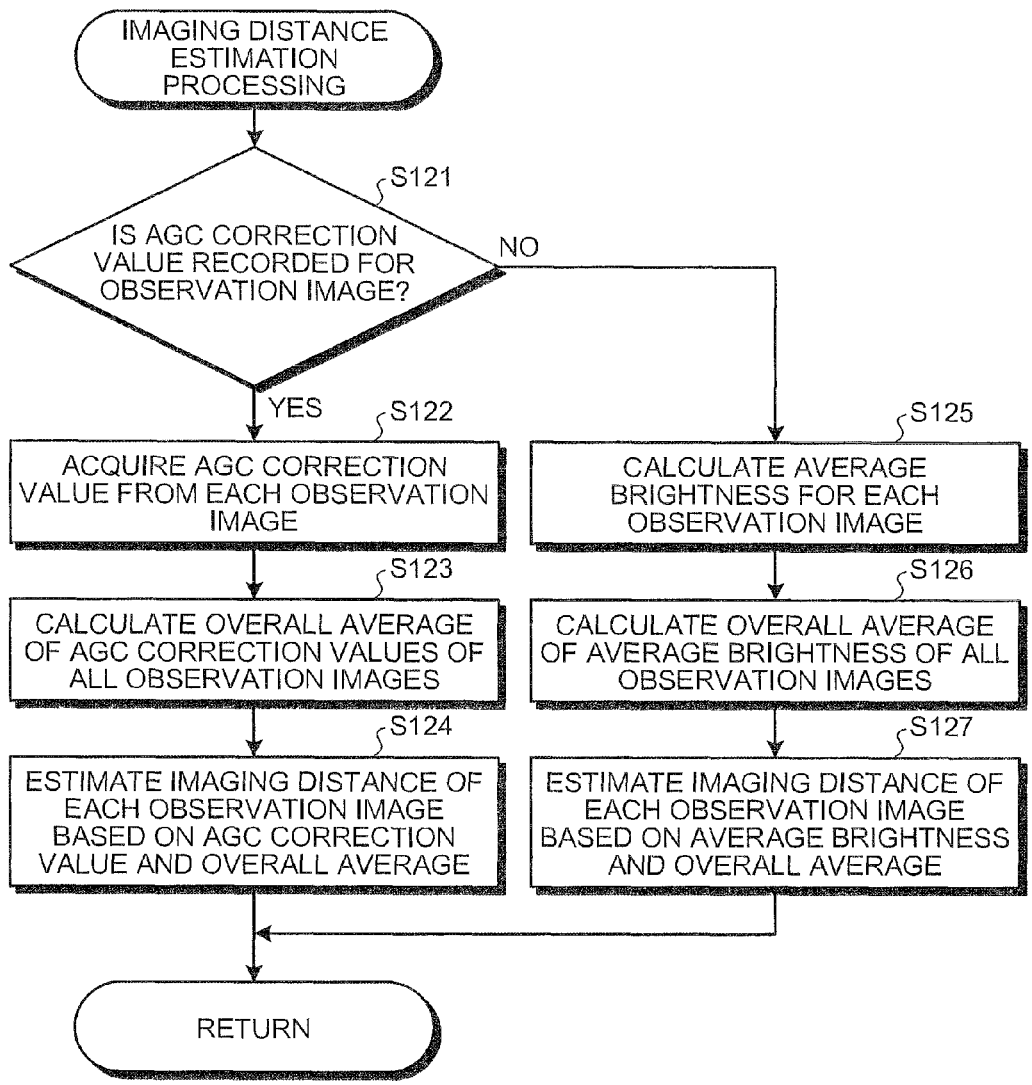
FIG. 6 is a flowchart of imaging distance estimation procedures.

FIG. 6 is a flowchart of processing procedures of the imaging distance estimation processing by the imaging distance estimation unit 4b. As shown in FIG. 6, the imaging distance estimation unit 4b determines whether the AGC correction value is recorded for the observation image (step S121). When the AGC correction value is recorded, the imaging distance estimation unit 4b estimates the imaging distance based on the AGC correction value, and when the AGC correction value is not recorded, the imaging distance estimation unit 4b estimates the imaging distance based on the average brightness.

Specifically, when the AGC correction value is recorded for the observation image (Yes in step S121), the imaging distance estimation unit 4b acquires the AGC correction value from each observation image (step S122), calculates the overall average of the AGC correction values of all the observation images (step S123), and estimates the imaging distance of each observation image based on the AGC correction value and the overall average (step S124).

On the other hand, when the AGC correction value is not recorded for the observation image (No in step S121), the imaging distance estimation unit 4b calculates the average brightness of each observation image (step S125), calculates the overall average of the average brightness of all the observation images (step S126), and estimates the imaging distance of each observation image based on the average brightness and the overall average (step S127). Then, the imaging distance estimation unit 4b, after performing step S124 or S127, finishes the imaging distance estimation processing and returns to step S103.

In step S124, the imaging distance estimation unit 4b estimates imaging distance X of a target image among the sequence of observation images according to following equation (1) based on AGC correction value C and overall average $C_{ave}$ thereof. Further, the imaging distance estimation unit 4b sequentially switches the target image from one image to another among the sequence of observation images and performs the same operation on the target image, thereby estimating the imaging distance of each observation image. In the equation (1), coefficient $f(C_{ave})$ is determined by a predetermined operation based on the overall average $C_{ave}$.

[Equation 1]

$$X = f(C_{ave})\sqrt{(1/C)} \quad (1)$$

In step S127, the imaging distance estimation unit 4b estimates the imaging distance X of a target image among the sequence of observation images according to following equation (2) based on average brightness E and overall average $E_{ave}$ thereof. The imaging distance estimation unit 4b sequentially switches the target image from one image to another among the sequence of observation images, and performs the same operation on the target image, thereby estimating the imaging distance of each observation image. In the equation (2), coefficient $f(E_{ave})$ is determined by a predetermined operation based on the overall average $E_{ave}$.

[Equation 2]

$$X = f(E_{ave})\sqrt{(1/E)} \quad (2)$$

When the AGC correction value is recorded for the observation image, the imaging distance estimation unit 4b can estimate the imaging distance based both on the AGC correction value and the average brightness instead of using only the AGC correction value. In this case, the imaging distance estimation unit 4b can perform both the processing of steps S122 to S124 and the processing of steps S125 to S127, and for example, use an average value of the estimated imaging distances obtained by these sets of processing as a final estimation result.

In the parameter setting processing in step S104, the image processing control unit 6a sets a parameter value of the abnormality detection parameter for each observation image based on the organ determined in the organ determination processing in step S102 and the imaging distance estimated in the imaging distance estimation processing in step S103. Here, the abnormality detection parameter is one of process parameters employed by the abnormal region detection unit 4c for the abnormal region detection processing in step S105, and includes a parameter indicating a predetermined feature quantity of an abnormal region, a parameter indicating a pixel block size (processing unit pixel block size) which is a processing unit of the observation image, and the like.

In general, the feature of the image region which should be detected as the abnormal region is different depending on the type of organs, such as the stomach, small intestine, and large intestine. For example, a region size (largeness) of the abnormal region to be detected in the small intestine is smaller than the region size of the abnormal region to be detected in the stomach. Hence, if the same value is set for both the stomach and the small intestine as a lower threshold value of a determination reference for judging the region size, which is a feature quantity, at the detection of abnormal regions, an image region of a region size to be detected cannot be detected in the small intestine as the abnormal region, while an image region of a region size which does not need to be detected in the stomach may be erroneously detected as the abnormal region. However, when an appropriate lower threshold value is set independently for each of the stomach and the small intestine, an abnormal region of a characteristic size corresponding to each of the stomach and the small intestine can be securely detected, and further, an image region which does not need to be detected as an abnormal region can be excluded from detection target.

Meanwhile, even when an image of the same abnormal area is picked up in different observation images, if the imaging distance is different, the region size of the abnormal region in each observation image can be different. Specifically, as the imaging distance becomes longer, the region size of the abnormal region becomes smaller. Hence, if the same value is set as a lower threshold value of the region size regardless of the imaging distance at the time of detection of abnormal region, and if the imaging distance is long, the region size of the abnormal region to be detected can be too small to detect, whereas if the imaging distance is short, the feature image region of a region size which does not need to be detected can be erroneously detected as the abnormal region. However, when an appropriate value is set as the lower threshold value according to the imaging distance, the abnormal region to be detected can be securely detected regardless of the imaging distance, and the feature image region which does not need to be detected as an abnormal region can be excluded from detection target.

In view of the above, in the image processing apparatus 1, an appropriate lower threshold value of the region size is stored in advance in the abnormality detection parameter storage unit 3d as a parameter value of a size parameter, which is an abnormality detection parameter, corresponding to organ and imaging distance as shown in an example of FIG. 7. In the parameter setting processing of step S104, the image processing control unit 6a reads out a parameter value from the abnormality detection parameter storage unit 3d based on the organ determined by the organ determination unit 4a and the imaging distance estimated by the imaging distance estimation unit 4b for each observation image, and sets the read-out parameter value as the abnormality detection parameter.

Here, a parameter value indicating the region size of the abnormal region is described above as an example of the parameter value of the abnormality detection parameter stored in advance in the abnormality detection parameter storage unit 3d. However, the parameter value does not need to be interpreted as being limited to a value indicating the region size. For example, the parameter value can indicate another feature quantity of the abnormal region, such as a color. Further, the parameter value is not limited to a value indicating the feature quantity of the abnormal region, and can indicate, for example, a processing unit pixel block size of the observation image.

Further, the parameter value to be stored in advance is not limited to the parameter value of one type of parameter. Parameter values of plural abnormality detection parameters can be stored. In this case, the abnormality detection parameter storage unit 3d stores the parameter values corresponding to each of the plural abnormality detection parameters in a storage table as shown in FIG. 7, for example, and the image processing control unit 6a, in the parameter setting processing, reads out a parameter value of each abnormality detection parameter from a corresponding storage table, and sets the read-out parameter value.

In the abnormal region detection processing of step S105, the abnormal region detection unit 4c employs, for a target image among the sequence of observation images, the abnormality detection parameter for which the parameter value corresponding to the target image is set in the parameter setting processing of step S104, and detects a predetermined abnormal region in the target image. Specifically, the abnormal region detection unit 4c employs, for example, the size parameter for which a parameter value stored in the storage table shown in FIG. 7 is set, and detects an image region as an abnormal region if the image region is smaller than the region size indicated by the set parameter value and has a predetermined feature (such as a color) as the abnormal region. Further, the abnormal region detection unit 4c sequentially switches the target image from one image to another among the sequence of observation images, and performs the same processing on each target image, thereby detecting the desired abnormal region in each observation image.

The processing performed by the abnormal region detection unit 4c is not limited to the processing based on the size parameter, and the abnormal region detection processing can be performed based on various types of processing. For example, as described in Japanese Patent Application Laid-Open No. 2005-192880, it is possible to map each pixel in the target image or averaged pixel of the target image on a feature space based on color information thereof, perform clustering to identify a normal-area cluster and an abnormal-area cluster, and detect a pixel region belonging to the abnormal-area cluster as an abnormal region. In this case, the abnormal region detection unit 4c preferably performs the abnormal region detection processing using a color parameter, which is an abnormality detection parameter for which a parameter value indicating color information constituting the feature space (such as a color or chromaticity) is set. The abnormal detection parameter storage unit 3d preferably stores in advance a parameter value to be set as the color parameter corresponding to each organ and imaging distance.

Further, the abnormal region detection unit 4c can divide the target image into plural processing unit pixel blocks, and compare color information of each processing unit pixel block with a previously-prepared color reference of an abnormal area and a previously-prepared color reference of a normal area to detect the abnormal region as described in Published Japanese Translation of International Patent Application No. 2004-521693 (Kohyo). In this case, the abnormal region detection unit 4c preferably performs the abnormal region detection processing using the color parameter, the block size parameter, or both. Here, the color parameter is a parameter for which a parameter value indicating color, chromaticity, or the like of each color reference is set, and the block size parameter is the abnormality detection parameter for which a parameter value indicating the processing unit pixel block size is set. The abnormality detection parameter storage unit 3d preferably stores a parameter value to be set for the color parameter, the block size parameter, or both in advance corresponding to each organ and imaging distance.

When the imaging power is not equal for all the images, the capsule endoscope records power information as additional information of each observation image. The detection of abnormal region is preferably performed in consideration of power when the abnormal region detection processing is performed based on the size parameter, the block size parameter, or both as mentioned above.

As described above, because the image processing apparatus 1 according to the embodiment includes the organ determination unit 4a which determines an organ, which is an observation target whose image is picked up in a target image among the sequence of observation images, as one of the esophagus, stomach, small intestine, and large intestine, i.e., as one of predetermined one or more observation target, the abnormal region detection unit 4c which detects an abnormal region, which is a feature image region having a predetermined feature, in the target image using the abnormality detection parameter as a predetermined process parameter, and the image processing control unit 6a which sets a parameter value corresponding to the result of determination by the organ determination unit 4a as the abnormality detection parameter and causes the abnormal region detection unit 4c to detect the abnormal region using the abnormality detection parameter, improved detection accuracy can be achieved in securely detecting in the target image, the abnormal region as an image region corresponding to the abnormal area and the like that exhibits a different feature depending on the type of organ.

Further, since the image processing apparatus 1 includes the imaging distance estimation unit 4b which estimates the imaging distance at the time of image pickup of the target image, and the image processing control unit 6a sets a parameter value corresponding to the result of determination by the organ determination unit 4a and the result of estimation by the imaging distance estimation unit 4b as the abnormality detection parameter, and causes the abnormal region detection unit 4c to detect the abnormal region using the abnormality detection parameter, improved detection accuracy can be achieved in securely detecting in the target image, the abnormal region that exhibits a different feature depending on the type of organ and imaging distance.

Further, since the image processing apparatus 1 sequentially switches the target image from one image to another among the sequence of observation images, and detects the abnormal region in each target image, the abnormal region can be detected from each observation image included in the sequence of observation images.

Next, a first modification of the image processing apparatus according to the embodiment is described. In the organ determination processing described above, the organ determination unit 4a performs organ determination based on the frequency component information of the observation image represented by a power spectrum, for example. In the first modification, the organ determination is performed based on an amount of image information of the observation image.

In general, there is a relatively little unevenness inside the esophagus and the stomach. Therefore, in the observation image in which an image of the esophagus or the stomach is picked up, correlation between each pixel and its surrounding pixel is higher than that in the observation image of the small intestine or the large intestine. Hence, the organ determination unit 4a can determine whether the organ whose image is picked up in the observation image is one of the esophagus and the stomach, or one of the small intestine and the large intestine by finding the level of correlation.

In general, it is known that the level of correlation between each pixel and its surrounding pixel is represented by an amount of image information, which is represented by entropy. Entropy H(f) can be found by following equation (3) based on bit sequence r of surrounding pixels of a target pixel, and probability p(r;f) of the target pixel having pixel value f. In the equation (3), entropy H(f) is entropy of Markov source.

$$H(f) = -\log_2(p(r;f)) \quad (3)$$

When the operation is performed according to the equation (3) over the entire image, entropy H(f) corresponding to each pixel can be obtained. It can be said that when the value of entropy H(f) tends to be high over the entire image, the correlation between each pixel and its surrounding pixel is low in the image, whereas when the value of entropy H(f) is low, the correlation between each pixel and its surrounding pixel is high. The organ determination unit 4a of the first modification, utilizing this characteristic, calculates entropy H(f) of each observation image and determines whether the organ whose image is picked up in the observation image is one of the esophagus and the stomach, or one of the small intestine and the large intestine, based on the result of calculation.

FIG. 8 is a flowchart of processing procedures of the organ determination processing by the organ determination unit 4a of the first modification. As shown in FIG. 8, the organ determination unit 4a calculates the entropy of each observation image according to the equation (3) (step S211), calculates the overall average of the entropy of all the observation images (step S212), and determines the organ whose image is picked up in each observation image based on the entropy, the overall average of the entropy, and the organ determination reference data stored in advance in the organ determination reference data storage unit 3b (step S213). Thereafter, the organ determination unit 4a finishes the organ determination processing and returns to step S102.

Figures 9, 10:
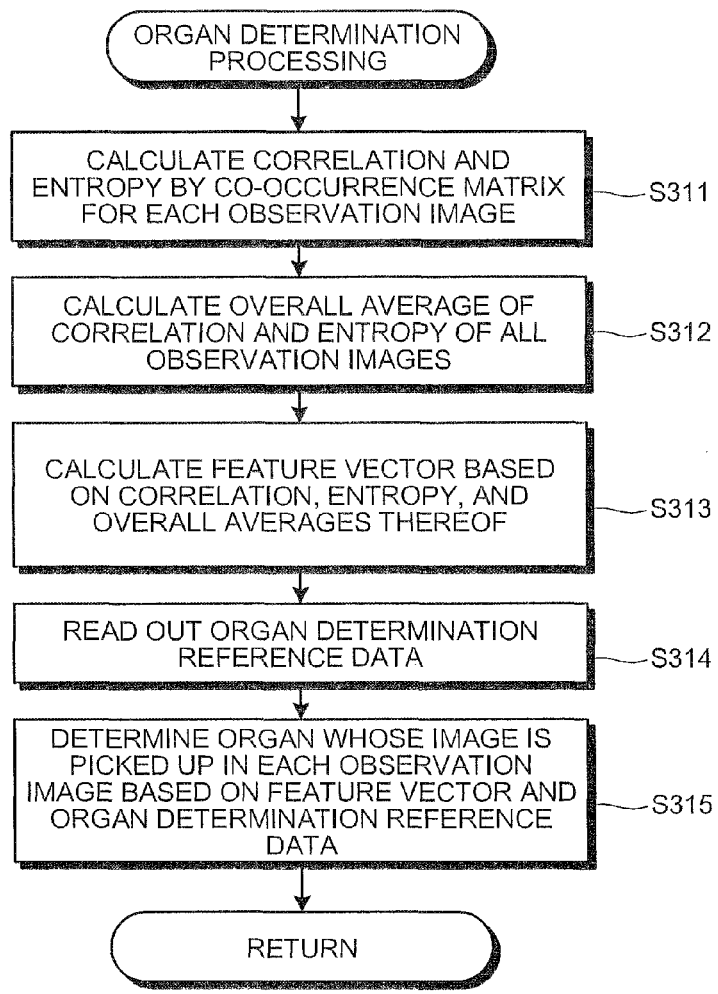
FIG. 9 is a table of organ determination reference data according to the first modification.
FIG. 10 is a flowchart of organ determination processing procedures according to a second modification.

Here, the organ determination reference data storage unit 3b stores therein a storage table as shown in FIG. 9 which associates the organ with the entropy and the overall average of the entropy as the organ determination reference data. The organ determination reference data can be created in advance based on the knowledge about each organ.

In step S213, the organ determination unit 4a determines that the organ whose image is picked up in the target image among the sequence of observation images is the one associated with the entropy and the overall average thereof in the organ determination reference data. For example, the organ determination unit 4a determines that the organ whose image is picked up in the target image is a small intestine according to the organ determination reference data shown in FIG. 9 if the entropy of the target image and the overall average of the entropy are both 0.2. Further, the organ determination unit 4a sequentially switches the target image from one image to another among the sequence of observation images, and performs the same processing on each target image, thereby determining the organ whose image is picked up in each observation image.

Next, a second modification of the image processing apparatus according to the embodiment is described. In the second modification, the organ determination unit 4a performs the organ determination based on texture information of the observation image. Generally, there is a relatively little unevenness inside the esophagus and the stomach. Therefore, the amount of texture information is small with respect to the observation image in which an image of the esophagus or the stomach appears. On the other hand, since the small intestine has many uneven patterns on its surface due to existence of villus and the like, a large amount of texture information is obtained for the observation image in which an image of the small intestine appears. Hence, the organ determination unit 4a can determine whether the organ whose image is picked up in the observation image is one of the esophagus and the stomach, or one of the small intestine and the large intestine based on the texture information of the observation image.

A method for finding a statistical feature quantity of texture as the texture information according to a co-occurrence matrix is generally known. The co-occurrence matrix is used for finding a feature quantity representing a property such as uniformity, directionality, and contrast of a pixel value based on a pixel value of a pair of pixels located at two separate points. As the second modification, a case where the correlation and the entropy are found as the texture information based on the co-occurrence matrix is described.

FIG. 10 is a flowchart of processing procedures of the organ determination processing by the organ determination unit 4a according to the second modification. As shown in FIG. 10, the organ determination unit 4a calculates the correlation and the entropy for each observation image according to a co-occurrence matrix (step S311), calculates an overall average of the correlation and an overall average of the entropy of all the observation images (step S312), and calculates a feature vector based on the calculated correlation, entropy, and overall average of each (step S313). Then, the organ determination unit 4a reads out the organ determination reference data from the organ determination reference data storage unit 3b (step S314), and determines the organ whose image is picked up in each observation image based on the calculated feature vector and the read-out organ determination reference data (step S315). Thereafter, the organ determination unit 4a finishes the organ determination processing and returns to step S102.

In step S311, the organ determination unit 4a calculates the correlation and the entropy for a target image among the sequence of observation images according to the co-occurrence matrix, sequentially switches the target image from one image to another among the sequence of observation images, and performs the same processing on each target image, thereby calculating a feature vector of each observation image.

In step S313, the organ determination unit 4a sets the correlation and the entropy calculated in step S311 and the overall average of each of the correlation and the entropy calculated in step S312 as a four-dimensional feature quantity for the target image among the sequence of observation images. Then, the organ determination unit 4a calculates a vector in a feature space represented by the four-dimensional feature quantity as a feature vector representing the texture information of the target image, and associates the vector with the target image. Further, the organ determination unit 4a sequentially switches the target image from one image to another among the sequence of observation images, and performs the same processing on the target image, to thereby calculate the feature vector of each observation image.

In step S314, the organ determination unit 4a reads out the organ determination reference data as a class dictionary in which each organ is classified in a four-dimensional feature space in advance. Then in step S315, the organ determination unit 4a determines the type of organ to which the feature vector calculated in step S313 for each observation image belongs based on the organ determination reference data read out in step S314 using a known judgment technique such as kNN method and subspace method. At the determination, the organ determination unit 4a sequentially switches the target image from one image to another among the sequence of observation images, and determines for each target image the type of organ to which the feature vector belongs. Thus, the organ determination unit 4a determines the organ whose image is picked up in each observation image as one of the esophagus and the stomach, or one of the small intestine and the large intestine, and associates the result of determination with each observation image.

In the above, the organ determination is described as being performed based on the feature vector whose feature quantities are the correlation calculated according to the co-occurrence matrix, the entropy, and the overall average of each. The feature quantities constituting the feature vector are not limited to the correlation and the entropy. Other feature quantities calculated according to the co-occurrence matrix can be similarly employed. Further, the feature quantity constituting the feature vector is not limited to four-dimensional quantities, and can be two-dimensional, five-dimensional, or more than five-dimensional. When the feature quantity is more than five-dimensional, more highly accurate organ determination can be performed. However, when the feature quantity is more than five-dimensional, the processing time required for the organ determination increases. Therefore, it is preferable to appropriately set the number of dimensions according to desirable determination accuracy. As described above, the overall average is employed as the feature quantity constituting the feature vector because the features of organs are different in each individual subject and it is preferable to reduce the influence of the individual difference.

Next, a third modification of the image processing apparatus according to the embodiment is described. In the third modification, the organ determination unit 4a determines whether the organ whose image is picked up in each observation image is one of the esophagus and the stomach, or one of the small intestine and the large intestine based on a file size of compressed image data which is compression-coded data of the observation image. Generally, there is a relatively little unevenness inside the esophagus and the stomach. Therefore, the correlation between each pixel and its surrounding pixel is higher in the observation image of the esophagus or the stomach than in the observation image of the small intestine or the large intestine. The organ determination unit 4a determines whether the organ whose image is picked up in the observation image is one of the esophagus and the stomach, or one of the small intestine and the large intestine by determining the level of correlation based on a file size of compressed image data.

Further, the organ determination unit 4a determines whether the organ whose image is picked up in the observation image is a small intestine or a large intestine based on an amount of variation in the file size of the compressed image data of the observation image. In the large intestine, which is generally filled with feces and the like, if, for example, the capsule endoscope is employed for acquiring the observation images, the movement of the capsule endoscope stalls and the file size of the observation image does not change much over time. On the other hand, in the small intestine, the capsule endoscope can move more smoothly than in the large intestine, and therefore the file size of the observation image shows a notable change over time. The organ determination unit 4a, utilizing this characteristic, determines whether the observation target whose image is picked up in the observation image is a small intestine or a large intestine based on the amount of variation in the file size of the observation image over time.

FIG. 11 is a flowchart of organ determination processing procedures. As shown in FIG. 11, the organ determination unit 4a calculates a moving average of file size based on the file size of compressed image data of the sequence of observation images (step S411), and further calculates an overall average of files size (step S412). Further, the organ determination unit 4a calculates the amount of variation in file size between consecutive observation images in the sequence of observation images, calculates the moving average of the amount of variation in file size (step S413), and calculates the overall average of the amount of variation in file size (step S414). Then, the organ determination unit 4a determines which organ appears in each observation image based on the result of calculation in each of the steps S411 to S413 (step S415), finishes the organ determination processing, and returns to step S102.

Figure 12A:
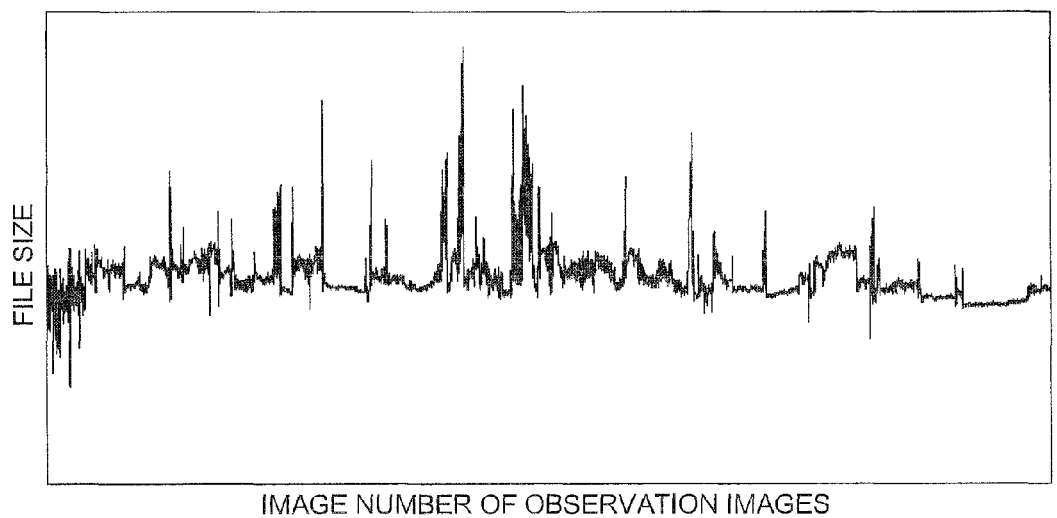
FIG. 12A is a graph of file size of a sequence of observation images.
Figure 12B:
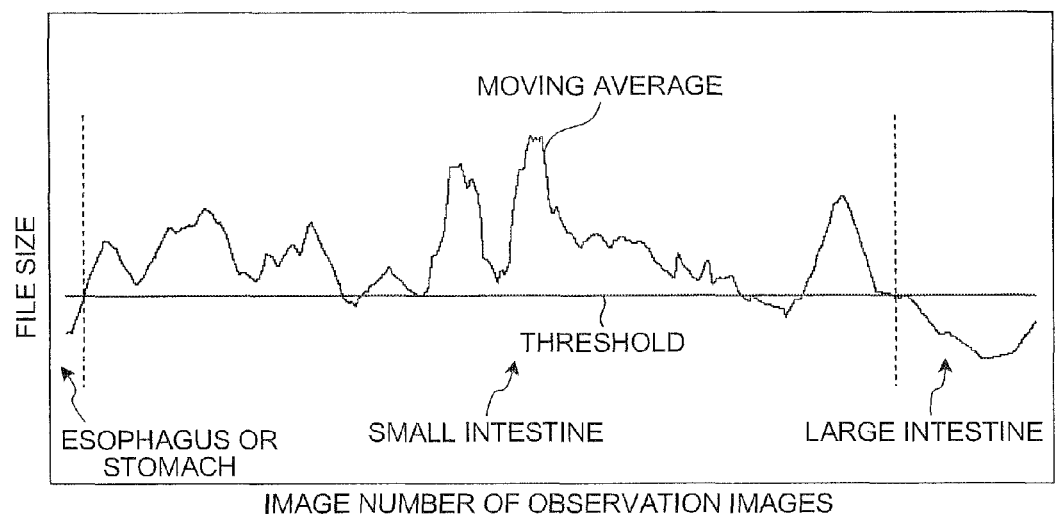
FIG. 12B is a graph of moving average of file size of the sequence of observation images.

In step S411, the organ determination unit 4a calculates for a target image in the sequence of observation images, a size average which is an average of file size of plural observation images including the target image and close to each other in time series. Then, the organ determination unit 4a associates the calculated size average with the target image. In the third modification, the size average is calculated based on, for example, a hundred observation images close to each other in time series in the sequence of observation images. The number of observation images used for the calculation of size average can be set as appropriate according to imaging intervals and the like of the image pickup of the sequence of observation images. The organ determination unit 4a sequentially switches the target image from one image to another among the sequence of observation images, and calculates the size average for each target image, to thereby obtain the moving average of the file size of the entire sequence of observation images. Specifically, in step S411, the organ determination unit 4a obtains the moving average of file size as shown in FIG. 12B based on file size information of the sequence of observation images shown in FIG. 12A.

Figure 12C:
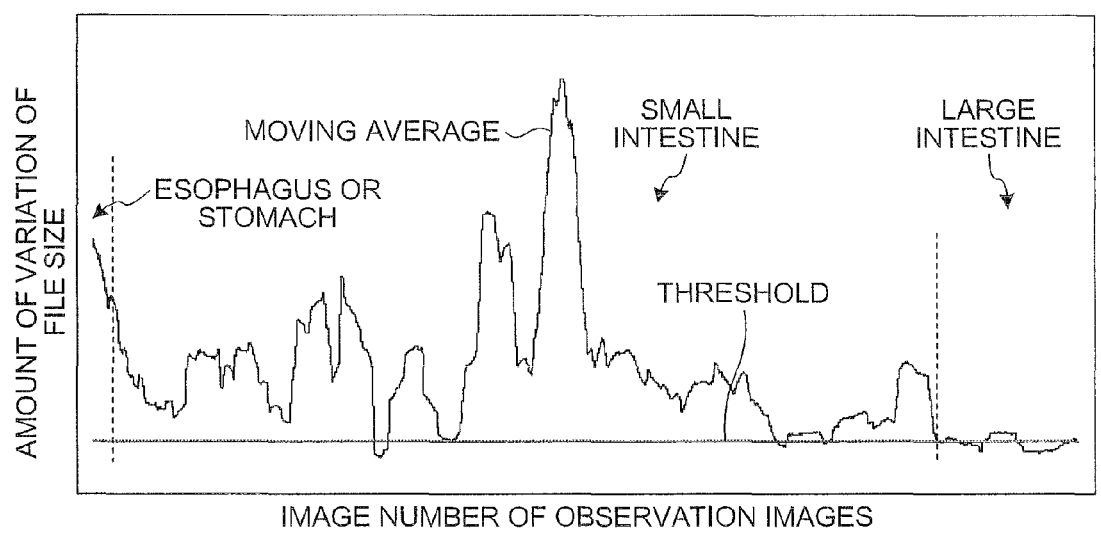
FIG. 12C is a graph of moving average of amount of variation in file size of the sequence of observation images.

In step S413, the organ determination unit 4a calculates for the target image in the sequence of observation images, an average amount of variation which is an average of the amount of variation in file size between observation images in plural observation images including the target image and close to each other in time series. Then, the organ determination unit 4a associates the calculated average amount of variation with the target image. In the third modification, the average amount of variation is calculated based on, for example, a hundred observation images close to each other in time-series in the sequence of observation images. The number of observation images used for the calculation of the average amount of variation may be set to an appropriate number according to imaging intervals of image pickup of the sequence of observation images. The organ determination unit 4a sequentially switches the target image from one image to another among the sequence of observation images, calculates the average amount of variation of each target image, and thereby obtains the moving average of the amount of variation in file size over the entire sequence of observation images. Specifically, in step S413, the organ determination unit 4a obtains moving averages of the amount of variation in file size as shown in FIG. 12C, based on the file size information of the sequence of observation images shown in FIG. 12A, for example.

In step S415, the organ determination unit 4a determines whether the organ whose image is picked up in a target image is one of the esophagus and the stomach, or one of the small intestine and the large intestine based on the size average calculated in step S411 and magnitude relation with the predetermined size determination reference for the target image in the sequence of observation images. Specifically, the organ determination unit 4a calculates threshold $T_{Fsize}$ as the size determination reference according to following equation (4) based on overall average $F_{sizeAve}$ calculated in step S412 and variable M set in advance (see FIG. 12B), and determines whether the size average $F_{size}$ satisfies following equation (5) with respect to the threshold $T_{Fsize}$.

$$T_{Fsize} = F_{sizeAve} + M \quad (4)$$

$$F_{size} < T_{Fsize} \quad (5)$$

The organ determination unit 4a determines that the organ whose image is picked up in the target image is one of the esophagus and the stomach when the equation (5) is satisfied, whereas determines that the organ is one of the small intestine and the large intestine when the equation (5) is not satisfied. Then, the organ determination unit 4a associates the result of determination with the target image. Further, the organ determination unit 4a sequentially switches the target image from one image to another among the sequence of observation images, and performs the same determination process to each target image, to thereby determine whether the organ whose image is picked up in each observation image among the sequence of observation images is one of the esophagus and the stomach, or one of the small intestine and the large intestine.

When it is obvious that, in the sequence of observation images, images of organs are picked up sequentially in the order of the stomach, small intestine, and large intestine, the organ determination unit 4a sequentially switches the target image starting from the starting image of the sequence. When the organ determination unit 4a comes to an image for which the equation (5) is not satisfied for the first time, the organ determination unit 4a determines that all subsequent observation images are images of one of the small intestine and the large intestine. Thus, the organ determination unit 4a can quickly distinguish the observation images of the esophagus and the stomach, from the observation images of the small intestine and the large intestine.

Then, the organ determination unit 4a determines whether the organ whose image is picked up in the target image is a small intestine or a large intestine based on the average amount of variation calculated in step S413 and magnitude relation with a predetermined variation amount determination reference for the target image which is determined to be the image of one of the small intestine and the large intestine among the sequence of observation images. Specifically, the organ determination unit 4a calculates threshold $T_{FsizeDiff}$ as the variation amount determination reference according to following equation (6) based on overall average $F_{sizeDiffAve}$ calculated in step S414 and variable N set in advance (see FIG. 12C), and determines whether the average amount of variation $F_{sizeDiff}$ satisfies following equation (7) with respect to the threshold $T_{FsizeDiff}$.

$$T_{FsizeDiff} = F_{sizeDiffAve} + N \quad (6)$$

$$F_{sizeDiff} < T_{FsizeDiff} \quad (7)$$

The organ determination unit 4a determines that the organ whose image is picked up in the target image is a large intestine when the equation (7) is satisfied, and that the organ is a small intestine when the equation (7) is not satisfied. Then, the organ determination unit 4a associates the result of determination with the target image. Further, the organ determination unit 4a sequentially switches the target image from one image to another among the observation images that are previously determined to be the images of small intestine or large intestine in the sequence of observation images, and performs the same determination process for each target image, to thereby determine whether the organ whose image is picked up in each observation image is a small intestine or a large intestine. Thus, the organ determination unit 4a can determine the organ whose image is picked up in each observation image in the sequence of observation images to be one of the esophagus, stomach, small intestine, and large intestine, and associate the result of determination with each observation image.

As shown in the equation (4), overall average $F_{sizeAve}$ of the file size is employed in the calculation of threshold $T_{Fsize}$ as the size determination reference, because the features of organs are different in each individual subject and it is preferable to reduce the influence of the individual difference. Similarly, as shown in the equation (6), overall average $F_{sizeDiffAve}$ of the amount of variation in file size is employed in the calculation of threshold $T_{FsizeDiff}$ as the variation amount determination reference so that the influence of individual difference can be reduced. Further, the variables M and N are set by an observer through an input from the input unit 2, and changeable as appropriate.

In the above described organ determination processing, the organ determination unit 4a collectively determines the organ whose image is picked up in each observation image in step S415. Alternatively, however, the organ determination unit 4a can perform the determination according to the equation (5) and the determination according to the equation (7) separately. For example, the organ determination unit 4a can perform the determination according to the equation (5) immediately after the step S412 so that the processing of step S413 is performed only for the observation image which is determined to be the image of a small intestine or a large intestine. Thus, the organ determination processing can be performed more quickly.

Further, in the above described organ determination processing, the organ determination unit 4a is described as sequentially performing the determination according to the equation (5) and the determination according to the equation (7) in step S415. Alternatively, however, the organ determination unit 4a can perform the determinations collectively. For example, the organ determination unit 4a can find a feature vector ($F_{size}$, $F_{sizeDiff}$) represented by the size average $F_{size}$ and the average amount of variation $F_{sizeDiff}$ of each target image, and determines the organ according to a region in the feature space to which the feature vector belongs. Specifically, when the feature vector ($F_{size}$, $F_{sizeDiff}$) is in a region which satisfies the equation (5), the organ determination unit 4a can determine that the organ whose image is picked up in the image is one of the esophagus and the stomach, and when the feature vector is in another region which satisfies the equation (7), the organ determination unit 4a can determine that the organ in the image is a large intestine. Further, when the feature vector is in the other region, the organ determination unit 4a can determine that the organ in the image is a small intestine.

Further, in the above-described organ determination processing, the organ determination unit 4a performs determination of the organ based on the size average of file size of plural observation images and the average amount of variation. However, it is not always necessary to employ the average, and the organ determination can be performed based on the file size of each image and the variation amount of file size of each image, for example. Thus, the organ determination processing can be performed more quickly when the required determination accuracy is relatively low.

Next, a fourth modification of the image processing apparatus according to the embodiment is described. In the fourth modification, the organ determination unit 4a performs the organ determination based on a DCT coefficient calculated at the decompression of compressed image data and a variation amount thereof.

Generally, the surface of the mucosal membrane of the esophagus and the stomach has a relatively little unevenness and is flat in comparison with that of the small intestine. On the other hand, the surface of small intestine is significantly uneven due to the existence of villus and the like. Hence, the low frequency component is dominant in the observation image of the stomach, whereas the high frequency component is dominant in the observation image of the small intestine. In the fourth modification, the organ determination unit 4a, utilizing this characteristic, determines whether the organ whose image is picked up in the observation image is one of the esophagus and the stomach, or one of the small intestine and the large intestine. Specifically, when the sequence of observation images is stored as compressed image data in DCT compression coding scheme such as JPEG, the organ determination unit 4a performs determination based on plural DCT coefficients which are obtained at the time of decompression of the compressed image data through inverse DCT.

In the large intestine, which is generally filled with feces and the like, if, for example, the capsule endoscope is employed for acquiring the observation images, the movement of the capsule endoscope stalls and the frequency component of the observation image does not change much over time. On the other hand, in the small intestine, the capsule endoscope can move more smoothly than in the large intestine, and therefore the frequency component of the observation image shows a notable change over time. The organ determination unit 4a, utilizing this characteristic, determines whether the organ whose image is picked up in the observation image is a small intestine or a large intestine based on the amount of variation in the frequency component of the observation image over time. Specifically, the organ determination unit 4a performs determination based on the amount of variation of DCT coefficients between the observation images consecutive in time-series when the sequence of observation images are stored as the compressed image data in the DCT compression coding scheme.

A method of finding power spectrum according to Fourier Transform is generally well known as a method of obtaining frequency component information of an image. The Fourier Transform, however, includes a large amount of computing processes, and generally requires enormous processing time. On the other hand, when the DCT coefficients are employed for the judgment of the frequency components, since the DCT coefficients can be calculated at the time of decompression of compressed image data, no specific computing process is required for the judgment of frequency components. In addition, the process of calculating the DCT coefficient itself is simple and requires only a short time. Thus, the judgment of the frequency components of the observation image and the determination of organ whose image is picked up in the observation image can be performed more quickly than when the power spectrum is employed based on the Fourier Transform.

FIG. 13 is a flowchart of the organ determination processing procedures. As shown in FIG. 13, the organ determination unit 4a calculates a representative DCT coefficient as a weighted average of DCT coefficients for each observation image (step S510). Then, the organ determination unit 4a calculates moving average of the representative DCT coefficient based on the representative DCT coefficients of the sequence of observation images (step S511), and calculates overall average of the representative DCT coefficients (step S512). Further, the organ determination unit 4a calculates the amount of variation of the representative DCT coefficients between observation images consecutive in the sequence of observation images, calculates moving average of the amount of variation of the representative DCT coefficient (step S513), and calculates overall average of the amount of variation of the representative DCT coefficient (step S514). Thereafter, the organ determination unit 4a determines the organ whose image is picked up in each observation image based on the result of calculations in steps S511 to S513 (step S515), finishes the organ determination processing, and returns to step S102.

In step S510, the organ determination unit 4a calculates a block average of each 8×8 pixel block, which is a processing unit in the decompression of compressed image data, based on predetermined plural DCT coefficients covering a range from a low frequency component to a high frequency component for each observation image. Specifically, based on DCT coefficients "DCT1" to "DCT64" of an 8×8 pixel block obtained as shown in FIG. 14, the organ determination unit 4a excludes "DCT1" which corresponds to a DC component, and calculates a weighted average of each frequency of all of "DCT2" to "DCT64", or a weighted average of each frequency of previously-selected one or more of the DCT coefficients among "DCT2" to "DCT64", as block average. When weighting for each frequency, the weight is preferably set heavier for higher frequency. Further, the organ determination unit 4a calculates overall average by averaging the block averages of the 8×8 pixel blocks for each observation image as a representative DCT coefficient.

In step S511, the organ determination unit 4a calculates, for a target image in the sequence of observation images, a DCT coefficient average, which is an average of representative DCT coefficients of plural observation images including the target image and close with each other in time-series. Then, the organ determination unit 4a associates the calculated DCT coefficient average with the target image. In the fourth modification, the organ determination unit 4a calculates the DCT coefficient average using, for example, one hundred observation images close with each other in time-series in the sequence of observation images. The number of observation images employed for the calculation of DCT coefficient average may be set to an appropriate number according to imaging interval of the image pickup of the sequence of observation images. The organ determination unit 4a sequentially switches the target image from one image to another among the sequence of observation images, calculates the DCT coefficient average for each target image, and thereby obtains moving average of the representative DCT coefficients over the entire sequence of observation images.

In step S513, the organ determination unit 4a calculates a DCT variation amount average, which is an average of amount of variation of the representative DCT coefficients between observation images in plural observation images including the target image and close to each other in time-series, with respect to the target image in the sequence of observation images. Then, the organ determination unit 4a associates the calculated DCT variation amount average with the target image. In the fourth modification, the organ determination unit 4a calculates the DCT variation amount average using, for example, a hundred observation images close to each other in time-series in the sequence of observation images. The number of observation images employed for the calculation of DCT variation amount average may be set to an appropriate number according to the imaging interval of image pickup of the sequence of observation images, for example. The organ determination unit 4a sequentially switches the target image from one image to another among the sequence of observation images, calculates the DCT variation amount average for each target image, and thereby obtains the moving average of the variation amount of representative DCT coefficients over the entire sequence of observation images.

In step S515, the organ determination unit 4a determines whether the organ whose image is picked up in the target image is one of the esophagus and the stomach, or one of the small intestine and the large intestine based on the DCT coefficient average calculated in step S511 and magnitude relation with a predetermined DCT determination reference for the target image in the sequence of observation images. Specifically, the organ determination unit 4a calculates threshold $T_{dct}$ as the DCT determination reference according to following equation (8) based on overall average $F_{dctAve}$ calculated in step S512 and variable K set in advance, and determines whether DCT coefficient average $F_{dct}$ satisfies following equation (9) with respect to the threshold TdCt.

$$T_{dct} = F_{dctAve} + K \quad (8)$$

$$F_{dct} < T_{dct} \quad (9)$$

The organ determination unit 4a determines that the organ whose image is picked up in the target image is one of the esophagus and the stomach when the equation (9) is satisfied, whereas determines that the organ is one of the small intestine and the large intestine when the equation (9) is not satisfied. Then, the organ determination unit 4a associates the result of determination with the target image. Further, the organ determination unit 4a sequentially switches the target image from one image to another among the sequence of observation images, performs the same determination on each target image, and thereby determines whether the organ whose image is picked up in each observation image among the sequence of observation images is one of the esophagus and the stomach, or one of the small intestine and the large intestine.

When it is obvious that the images of organs are picked up in the sequence of observation images in the order of the stomach, small intestine, and large intestine, the organ determination unit 4a sequentially switches the target image starting from the starting image, and when it first comes across the observation image which does not satisfies the equation (9), the organ determination unit 4a determines that all subsequent observation images are images of one of the small intestine and the large intestine. Thus, the organ determination unit 4a can quickly distinguish the observation images of one of the esophagus and the stomach from the observation images of one of the small intestine and the large intestine.

Then, the organ determination unit 4a determines whether the organ whose image is picked up in the target image is a small intestine or a large intestine based on the DCT variation amount average calculated in step S513 and the magnitude relation with a predetermined DCT variation amount determination reference for the target image included in the sequence of observation images determined to be the images of one of the small intestine and the large intestine. Specifically, the organ determination unit 4a calculates threshold $T_{dctDiff}$ as the DCT variation amount determination reference according to following equation (10) based on overall average $F_{dctDiffAve}$ calculated in step S514 and variable L set in advance, and determines whether the DCT variation amount average $F_{dctDiff}$ satisfies following equation (11) with respect to the threshold $T_{dctDiff}$.

$$T_{dctDoff} = F_{dctDiffAve} + L \qquad (10)$$

$$F_{dctDiff} < T_{dctDiff} \qquad (11)$$

When the equation (11) is satisfied, the organ determination unit 4a determines that the organ whose image is picked up in the target image is a large intestine, whereas determines that the organ is a small intestine when the equation (11) is not satisfied. Then, the organ determination unit 4a associates the result of determination with the target image. Further, the organ determination unit 4a sequentially switches the target image from one image to another among the observation images previously determined to be the images of one of the small intestine and the large intestine, performs the same determination processing on each target image, and thereby determines whether the organ whose image is picked up in each observation image is a small intestine or a large intestine. Thus, the organ determination unit 4a can determine the organ whose image is picked up in each observation image in the entire sequence of observation images as one of the esophagus, stomach, small intestine, and large intestine, and associate the result of determination with each observation image.

As shown in the equation (8), the overall average $F_{dctAve}$ of the representative DCT coefficients is employed for the calculation of threshold $T_{dct}$ which serves as the DCT determination reference because the features of the organs are different in each individual subject and it is preferable to reduce the influence of individual difference. Similarly, as shown in the equation (10), the overall average $F_{dctDiffAve}$ of the amount of variation of the representative DCT coefficients is employed for the calculation of the threshold $T_{dctDiff}$ which serves as the DCT variation amount determination reference so that the influence of individual difference can be reduced. Further, variables K and L are set by the observer via the input unit 2 and are changeable as appropriate.

In the organ determination processing described above, the organ determination unit 4a collectively determines the organs whose image is picked up in each observation image in step S515. Alternatively, however, the organ determination unit 4a can perform the determination based on the equation (9) and the determination based on the equation (11) separately. For example, if the determination based on the equation (9) is performed immediately after step S512, step S513 can be performed only on the observation image determined to be the image of one of the small intestine and the large intestine. Thus, the organ determination processing can be performed more quickly.

In the organ determination processing described above, the organ determination unit 4a is described as sequentially performing the determination based on the equation (9) and the determination based on the equation (11) in step S515. The organ determination unit 4a can, however, perform these determination processes collectively. For example, it is possible to find a feature vector ($F_{dct}$, $F_{dctDiff}$) represented by the DCT coefficient average $F_{dct}$ and the DCT variation amount average $F_{dctDiff}$ for each target image, and determine the organ according to a region in a feature space to which the found feature vector belongs. Specifically, when the feature vector ($F_{dct}$, $F_{dctDiff}$) is within a region satisfying the equation (9), the organ determination unit 4a determines that the organ in the target image is one of the esophagus and the stomach. When the feature vector is in another region which satisfies the equation (11), the organ determination unit 4a can determine that the organ in the target image is a large intestine. When the feature vector is in the other area, the organ determination unit 4a can determine that the organ in the target image is a small intestine.

In the organ determination processing described above, the organ determination unit 4a determines the organ based on the DCT coefficient average and the DCT variation amount average in plural observation images. It is not necessary, however, to use the average all the time. For example, the organ determination can be performed based on the representative DCT coefficient of each observation image and the variation amount of representative DCT coefficient of each observation image. Thus, when the required determination accuracy is relatively low, the organ determination processing can be performed more quickly.

A fifth modification of the image processing apparatus according to the embodiment is described. In the fifth modification, the organ determination unit 4a performs the organ determination by finding a feature vector based on plural DCT coefficients of each observation image and using the found feature vector.

Figure 15:
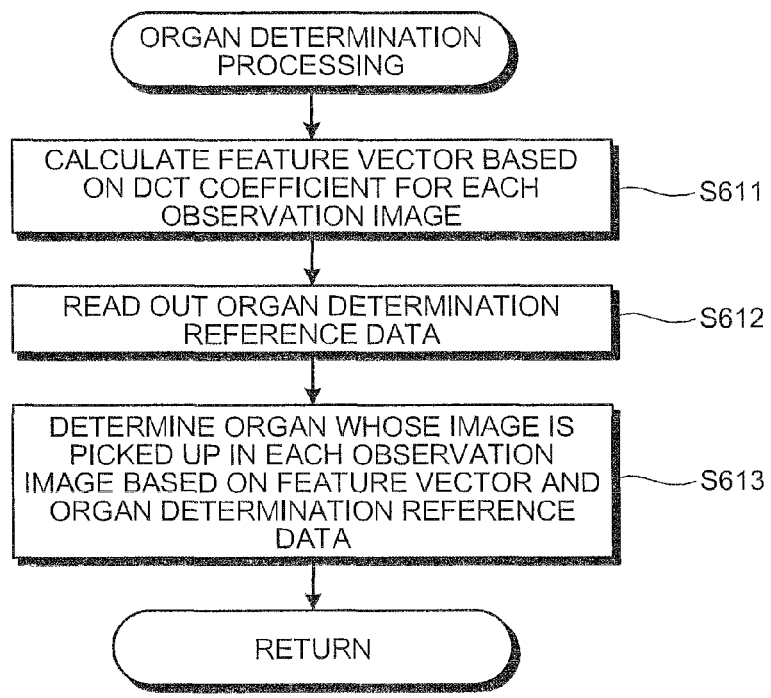
FIG. 15 is a flowchart of organ determination processing procedures according to a fifth modification.

FIG. 15 is a flowchart of processing procedures of the organ determination processing by the organ determination unit 4a. As shown in FIG. 15, the organ determination unit 4a calculates a feature vector of each observation image based on the DCT coefficients (step S611), and reads out the organ determination reference data from the organ determination reference data storage unit 3b (step S612). Then, the organ determination unit 4a determines the organ whose image is picked up in each observation image based on the calculated feature vector and the read-out organ determination reference data (step S613), finishes the organ determination processing, and returns to step S102.

In step S611, the organ determination unit 4a calculates a block representative value of a low frequency component and a block representative value of a high frequency component based on predetermined one or more DCT coefficients for each 8×8 pixel block, which is a processing unit in decompression of compressed image data, for the target image included in the sequence of observation images. Specifically, the organ determination unit 4a calculates a weighted average of "DCT2" to "DCT10" for each frequency as the block representative value of the low frequency component based on the DCT coefficients "DCT1" to "DCT64" of the 8×8 pixel block obtained as shown in FIG. 14, and calculates a weighted average of "DCT55" to "DCT64" for each frequency as the block representative value of the high frequency component. When weighting for each frequency, the weight is preferably set heavier for higher frequency.

Further, the organ determination unit 4a calculates the average of each of the block representative value of the low frequency component, the block representative value of the high frequency component, and "DCT1" which is a DC component, over the entire 8×8 pixel blocks in the target image, as feature quantities D, E, and F. Then, the organ determination unit 4a associates a vector represented by the feature quantities D, E, and F in the feature space with the target image as the feature vector representing the frequency distribution of the target image. Further, the organ determination unit 4a sequentially switches the target image from one image to another among the sequence of observation images, and performs the same processing on each target image, thereby calculating the feature vector of each observation image.

Figure 16:
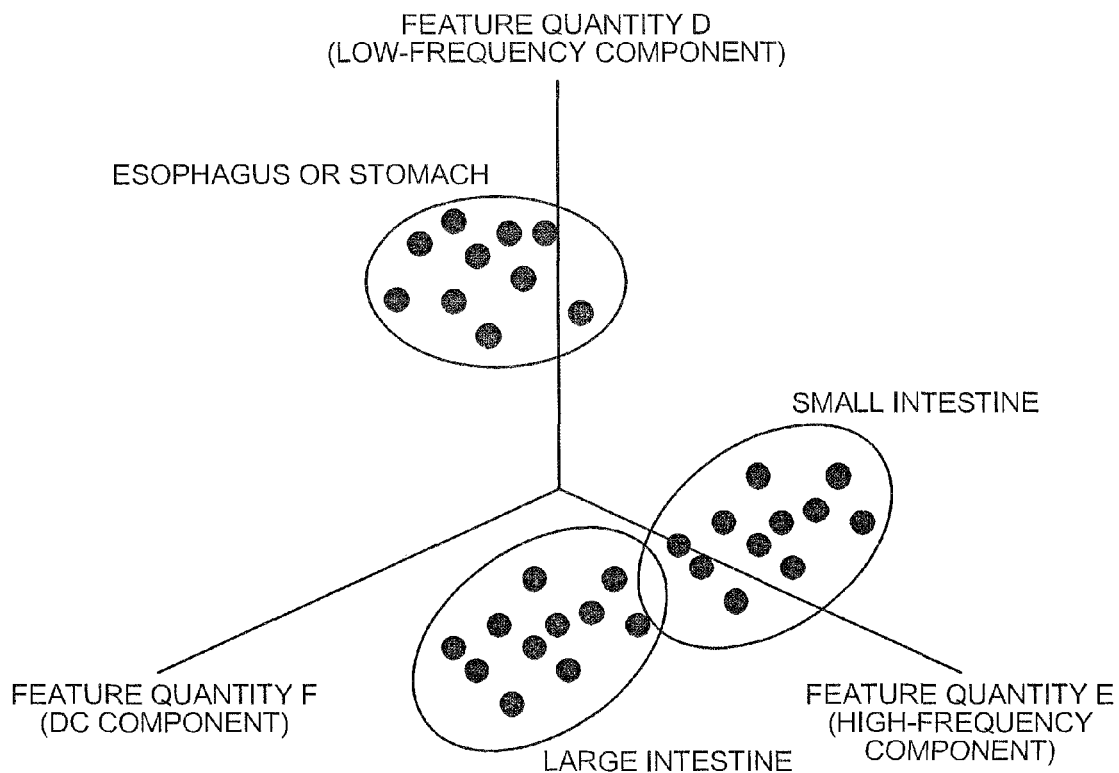
FIG. 16 is a diagram for explaining organ determination reference data.

In step S612, the organ determination unit 4a reads out the organ determination reference data as a class dictionary in which organs are classified in advance on the feature space as shown in FIG. 16. Then, in step S613, the organ determination unit 4a employs a known judgment technique such as kNN method (k-Nearest Neighbor Method) and subspace method, to determine the type of organ the feature vector calculated in step S611 for each observation image belongs based on the organ determination reference data read out in step S612. At the determination, the organ determination unit 4a sequentially switches the target image from one image to another among the sequence of observation images, and determines the type of organ the feature vector belongs for each target image. Thus, the organ determination unit 4a determines the organ whose image is picked up in each observation image to be one of the esophagus, stomach, small intestine, and large intestine, and associates the result of determination with each observation image.

In the organ determination processing described above, the organ determination unit 4a calculates the feature vector based on three feature quantities D, E, and F for organ determination. Here, the number of employed feature quantities is not limited to three, and two, four, or more feature quantities can be employed for the calculation of feature vector. For example, when the DCT coefficients "DCT1" to "DCT64" are each set as the block representative value for each 8×8 pixel blocks and the average of each set block representative value across all the 8×8 pixel blocks in the target image is calculated as the feature quantity in step S611, a feature vector consisting of feature quantities of 64 dimensions at maximum can be obtained. Thus, the organ determination can be performed based on a feature vector reflecting all the frequency components with respect to the DCT coefficients, and more accurate organ determination can be performed. When the number of dimensions increases, however, the processing time required for the calculation of feature vector increases. Therefore, it is preferable to set the number of dimensions appropriately according to the required determination accuracy.

The exemplary embodiments of the present invention including the first to the fifth modifications have been described. The present invention, however, is not limited to the exemplary embodiments described above, and various modifications can be made without departing from the scope of the present invention.

For example, in the embodiment described above, the image processing control unit 6a sets the parameter value of the abnormality detection parameter based on the organ determined by the organ determination unit 4a and the imaging distance estimated by the imaging distance estimation unit 4b. The parameter value can, however, be set based on one of the organ determined by the organ determination unit 4a and the imaging distance estimated by the imaging distance estimation unit 4b.

In this case, the abnormality detection parameter storage unit 3d may be provided with a storage table storing in advance parameter values corresponding to the organs or the imaging distances. Specifically, the abnormality detection parameter storage unit 3d may be provided with a storage table storing parameter values for each organ as shown in FIG. 17A when the image processing control unit 6a sets the parameter value based on the organ. Further, when the image processing control unit 6a sets the parameter value based on the imaging distance, the abnormality detection parameter storage unit 3d may be provided with a storage table storing parameter values corresponding to imaging distances as shown in FIG. 17B.

Further, when the image processing control unit 6a sets the parameter values based only on one of the organ and the imaging distance, the image processing unit 4 may include only the organ determination unit 4a or the imaging distance estimation unit 4b, and the storage unit 3 may include only the organ determination reference data storage unit 3b or the distance estimation reference data storage unit 3c. Then, in the image processing procedures shown in FIG. 2, the organ determination processing of step S102 or the imaging distance estimation processing of step S103 can be omitted.

Further, in the organ determination processing of the embodiment described above, the organ determination unit 4a is described as performing the organ determination for all the observation images in the sequence of observation images. Alternatively, however, the organ determination unit 4a can perform the organ determination only for the observation images of a previously designated number, or up to a previously designated image number. Alternatively, it is possible to designate a desired organ, and set the observation images up to an image in which the desired organ appears as the processing target. Thus, the organ determination processing can be performed only on the observation images of a desired organ still more quickly.

Similarly, in the imaging distance estimation processing, the parameter setting processing, and the abnormal region detection processing, only a previously designated number of observation images can be processed. Thus, the overall processing time required for the detection of abnormal region can be further reduced.

In the embodiments described above, the sequence of observation images processed by the image processing apparatus 1 are images obtained through sequential image pickup of interiors of the esophagus, stomach, small intestine, and large intestine. The present invention, however, is applicable to a group of images obtained through image pickup of one of esophagus, stomach, small intestine, and large intestine.

According to the image processing apparatus and the image processing program of the present invention, detection accuracy can be improved in securely detecting an image region, which shows different features depending on the type of observation targets, from a sequence of observation images in which an image of at least one of plural types of observation targets is individually picked up. Further, the image processing apparatus and the image processing program according to the present invention can improve the detection accuracy in securely detecting the image region, which shows different features depending on the imaging distances, from the sequence of observation images.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for detecting a feature image region, which is a specific region, from a sequence of observation images in which an image of at least one type of plural types of observation targets is picked up individually, comprising:

a target determination unit that determines a type of an observation target whose image is picked up in a target image among the sequence of observation images;

a region detection unit that detects the feature image region from the target image using a process parameter for detecting the feature image region;

a distance estimation unit that estimates an imaging distance at a time of image pickup of the target image; and a setting control unit that sets a parameter value corresponding to a result of determination by the target determination unit and a result of estimation by the distance estimation unit, as the process parameter, and causes the region detection unit to detect the feature image region using the process parameter.

2. The image processing apparatus according to claim 1, wherein
the target determination unit determines the type of the observation target whose image is picked up in the target image based on at least one type of information among compression information, frequency component information, an amount of image information, and texture information of the target image.

3. The image processing apparatus according to claim 1, wherein the parameter value represents one of a value defining a feature of the feature image region, and a processing unit pixel block size of the target image processed by the region detection unit.

4. The image processing apparatus according to claim 3, wherein
the value defining a feature is a region size or color.

5. The image processing apparatus according to claim 1, wherein
the distance estimation unit estimates the imaging distance at the time of image pickup of the target image based at least on brightness information or gain information of the target image.

6. The image processing apparatus according to claim 1, further comprising
a parameter storage unit that stores therein the parameter value corresponding to the type of observation target based on the imaging distance,
the setting control unit sets a parameter value corresponding to the type of observation target determined by the target determination unit and the imaging distance estimated by the distance estimation unit among the parameter values stored in the parameter storage unit, as the process parameter.

7. The image processing apparatus according to claim 1, wherein
the target determination unit sequentially switches the target image from one image to another among the sequence of observation images, and determines the observation target for each target image,
the region detection unit sequentially switches the target image from one image to another among the sequence of observation images and detects the feature image region of each target image.

8. The image processing apparatus according to claim 3, wherein
the distance estimation unit sequentially switches the target image from one image to another among the sequence of observation images and estimates the imaging distance of each target image.

9. The image processing apparatus according to claim 1, wherein at least one type of the observation targets is an interior of an organ included in a group of organs consisting of an esophagus, a stomach, a small intestine, and a large intestine, and the region detection unit detects as the feature image region, an abnormal area in the organ determined by the target determination unit.

10. An image processing apparatus for detecting a feature image region, which is a specific region, from a sequence of observation images in which an image of at least one type of plural types of observation targets is picked up individually, comprising:

a target determination unit that determines a type of an observation target whose image is picked up in a target image in the sequence of observation images;

a region detection unit that detects the feature image region in the target image using a process parameter for detecting the feature image region; and a setting control unit that sets a parameter value corresponding to a result of determination by the target determination unit as the process parameter, and causes the region detection unit to detect the feature image region using the process parameter.

11. The image processing apparatus according to claim 10, further comprising
a parameter storage unit that stores the parameter value corresponding to the type of the observation target in advance, and
the setting control unit sets as the process parameter, a parameter value, among the parameter values stored in the parameter storage unit, corresponding to the type of the observation target determined by the target determination unit.

12. A computer program product having a computer readable medium including programmed instructions for detecting a feature image region, which is a specific region, from a sequence of observation images in which an image of at least one type of plural types of observation targets is picked up individually, wherein the instructions, when executed by a computer, cause the computer to perform:

determining a type of an observation target whose image is picked up in a target image among the sequence of observation images;

setting a parameter value corresponding to a result of determination of the type of the observation target as a process parameter for detecting the feature image region; and detecting the feature image region from the target image using the process parameter set.

13. An image processing apparatus for detecting a feature image region, which is a specific region, from a sequence of observation images picked up at different imaging distances, comprising:

a distance estimation unit that estimates an imaging distance at a time of image pickup of a target image among the sequence of observation images;

a region detection unit that detects the feature image region from the target image using a process parameter for detecting the feature image region; and a setting control unit that sets a parameter value corresponding to a result of estimation by the distance estimation unit as the process parameter, and causes the region detection unit to detect the feature image region using the process parameter.

14. The image processing apparatus according to claim 13, further comprising a parameter storage unit that stores a parameter value corresponding to the imaging distance in advance, and the setting control unit sets as the process parameter, a parameter value, among the parameter values stored in the parameter storage unit, corresponding to the imaging distance estimated by the distance estimation unit.

15. The image processing apparatus according to claim 13, wherein the parameter value represents one of a value defining a feature of the feature image region, and a processing unit pixel block size of the target image processed by the region detection unit.

16. The image processing apparatus according to claim 15, wherein the value defining a feature is a region size or chromaticity.

17. The image processing apparatus according to claim 13, wherein the distance estimation unit estimates the imaging distance at the time of image pickup of the target image based at least on brightness information or gain information of the target image.

18. The image processing apparatus according to claim 13, wherein the distance estimation unit sequentially switches the target image from one image to another among the sequence of observation images and estimates the imaging distance of each target image.

19. The image processing apparatus according to claim 13, wherein the sequence of observation images is a group of images in which an image of at least one organ included in a group of organs consisting of an esophagus, stomach, small intestine, and large intestine appears, and the region detection unit detects an abnormal area in the organ.

20. A computer program product having a computer readable medium including programmed instructions for detecting a feature image region, which is a specific region, from a sequence of observation images picked up at different imaging distances, wherein the instructions, when executed by a computer, cause the computer to perform:

estimating an imaging distance at a time of image pickup of a target image among the sequence of observation images;

setting a parameter value corresponding to a result of estimation of the imaging distance as a process parameter for detecting the feature image region; and detecting the feature image region from the target image using the process parameter.

\* \* \* \* \*